(12) United States Patent
Bloom et al.

(10) Patent No.: US 8,974,827 B2
(45) Date of Patent: Mar. 10, 2015

(54) NANOPARTICLES COMPRISING A NON-IONIZABLE CELLULOSIC POLYMER AND AN AMPHIPHILIC NON-IONIZABLE BLOCK COPOLYMER

(75) Inventors: Corey Jay Bloom, Bend, OR (US); Marshall David Crew, Bend, OR (US); Warren Kenyon Miller, Bend, OR (US); Michael Mark Morgen, Bend, OR (US); Daniel Tod Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 407 days.

(21) Appl. No.: 12/451,810

(22) PCT Filed: May 26, 2008

(86) PCT No.: PCT/IB2008/001352
§ 371 (c)(1),
(2), (4) Date: Apr. 21, 2010

(87) PCT Pub. No.: WO2008/149192
PCT Pub. Date: Dec. 11, 2008

(65) Prior Publication Data
US 2010/0323014 A1 Dec. 23, 2010

Related U.S. Application Data

(60) Provisional application No. 60/941,755, filed on Jun. 4, 2007.

(51) Int. Cl.
*A61K 9/14* (2006.01)
*A61K 9/00* (2006.01)
*A61K 31/47* (2006.01)
*A61K 31/42* (2006.01)
*A61K 31/415* (2006.01)
*A01N 43/40* (2006.01)
*A01N 43/80* (2006.01)
*A01N 43/56* (2006.01)
*A61K 9/51* (2006.01)
*A61K 31/435* (2006.01)
*A61K 47/34* (2006.01)
*A61K 47/38* (2006.01)

(52) U.S. Cl.
CPC ............ *A61K 9/5138* (2013.01); *A61K 9/5161* (2013.01); *A61K 9/5192* (2013.01); *A61K 31/415* (2013.01); *A61K 31/42* (2013.01); *A61K 31/435* (2013.01); *A61K 47/34* (2013.01); *A61K 47/38* (2013.01); *Y10S 977/773* (2013.01); *Y10S 977/906* (2013.01)
USPC ........... 424/486; 424/400; 424/484; 424/488; 514/313; 514/378; 514/406; 977/773; 977/906

(58) Field of Classification Search
CPC .... A61K 9/5161; A61K 9/1652; A61K 47/38
See application file for complete search history.

(56) References Cited

U.S. PATENT DOCUMENTS

| | | |
|---|---|---|
| 3,960,757 A | 6/1976 | Morishita et al. |
| 4,107,288 A | 8/1978 | Oppenheim et al. |
| 4,158,707 A | 6/1979 | Steffen |
| 4,229,360 A | 10/1980 | Schneider |
| 4,298,594 A | 11/1981 | Sears |
| 4,329,332 A | 5/1982 | Couvreur et al. |
| 4,331,654 A | 5/1982 | Morris |
| 4,501,726 A | 2/1985 | Schroder |
| 4,610,868 A | 9/1986 | Fountain et al. |
| 4,615,881 A | 10/1986 | Deibig et al. |
| 4,639,370 A | 1/1987 | Carli |
| 4,649,155 A | 3/1987 | Steffen |
| 4,725,442 A | 2/1988 | Haynes |
| 4,728,513 A | 3/1988 | Ventouras |
| 4,731,210 A | 3/1988 | Weder et al. |
| 4,754,027 A | 6/1988 | Applegren |
| 4,826,689 A | 5/1989 | Violanto |
| 4,830,858 A | 5/1989 | Payne |
| 4,837,381 A | 6/1989 | Steber et al. |
| 4,880,634 A | 11/1989 | Speiser |
| 4,882,164 A | 11/1989 | Ferro et al. |
| 4,904,479 A | 2/1990 | Illum |
| 4,917,900 A | 4/1990 | Jones et al. |
| 4,997,454 A | 3/1991 | Violante |
| 5,049,322 A | 9/1991 | Devissaguet et al. |
| 5,051,261 A | 9/1991 | McGinity |
| 5,084,278 A | 1/1992 | Mehta |
| 5,085,864 A | 2/1992 | Cannon et al. |
| 5,091,187 A | 2/1992 | Haynes |

(Continued)

FOREIGN PATENT DOCUMENTS

| | | |
|---|---|---|
| EP | 877033 A1 | 11/1998 |
| EP | 1180062 B1 | 3/2004 |
| EP | 710261 B1 | 5/2004 |
| WO | WO 9710811 A1 | 3/1997 |
| WO | WO 9713503 A1 | 4/1997 |
| WO | WO 9933558 A1 | 7/1999 |

OTHER PUBLICATIONS

Shuai et al. Bioconjug. Chem., 2004, 15, 441-448.*
Bodmeier et al. J. Control. Release, 1990, 12, 223-233 (IDS: submitted Dec. 22, 2010).*
Liggins et al. J. Pharm. Sci., 1997, 86 (12), 1458-1463.*
Celikkaya E et al, "Rifampicin carrying poly (D,L-lactide)/poly(ethylene glycol) microspheres: loading and release," Artificial Organs, Blackwell Scientific, vol. 20, No. 7, Jul. 1, 1996.

(Continued)

*Primary Examiner* — Gina Justice
*Assistant Examiner* — Genevieve S Alley
(74) *Attorney, Agent, or Firm* — Klarquist Sparkman, LLP

(57) ABSTRACT

A pharmaceutical composition comprises nanoparticles comprising a poorly water-soluble drug, a poorly aqueous soluble non-ionizable cellulosic polymer, and a poorly aqueous soluble polymeric amphiphilic non-ionizable block copolymer.

13 Claims, 1 Drawing Sheet

(56) References Cited

U.S. PATENT DOCUMENTS

| | | |
|---|---|---|
| 5,091,188 A | 2/1992 | Haynes |
| 5,112,621 A | 5/1992 | Stevens et al. |
| 5,118,528 A | 6/1992 | Fessi et al. |
| 5,133,908 A | 7/1992 | Stainmesse et al. |
| 5,145,684 A | 9/1992 | Liversidge et al. |
| 5,152,923 A | 10/1992 | Weder |
| 5,174,930 A | 12/1992 | Stainmesse et al. |
| 5,188,837 A | 2/1993 | Domb |
| 5,202,159 A | 4/1993 | Chen et al. |
| 5,298,262 A | 3/1994 | Na |
| 5,302,401 A | 4/1994 | Liversidge et al. |
| 5,314,506 A | 5/1994 | Midler et al. |
| 5,336,507 A | 8/1994 | Na |
| 5,340,591 A | 8/1994 | Nakano et al. |
| 5,352,459 A | 10/1994 | Hollister et al. |
| 5,370,880 A | 12/1994 | Jones et al. |
| 5,445,830 A | 8/1995 | Ishizue et al. |
| 5,456,923 A | 10/1995 | Nakamichi et al. |
| 5,470,583 A | 11/1995 | Na |
| 5,484,608 A | 1/1996 | Rudnic et al. |
| 5,494,683 A | 2/1996 | Liversidge et al. |
| 5,510,118 A | 4/1996 | Bosch et al. |
| 5,534,270 A | 7/1996 | De Castro |
| 5,543,158 A | 8/1996 | Gref et al. |
| 5,552,160 A | 9/1996 | Liversidge et al. |
| 5,556,642 A | 9/1996 | Kobayashi et al. |
| 5,560,931 A | 10/1996 | Eickhoff et al. |
| 5,560,932 A | 10/1996 | Bagchi et al. |
| 5,565,188 A | 10/1996 | Wong et al. |
| 5,565,215 A | 10/1996 | Gref et al. |
| 5,569,448 A | 10/1996 | Wong et al. |
| 5,569,469 A | 10/1996 | Lovrecich |
| 5,571,536 A | 11/1996 | Eickhoff et al. |
| 5,573,783 A | 11/1996 | Desieno |
| 5,576,016 A | 11/1996 | Amselem |
| 5,578,325 A | 11/1996 | Domb et al. |
| 5,585,108 A | 12/1996 | Ruddy et al. |
| 5,622,938 A | 4/1997 | Wong |
| 5,662,883 A | 9/1997 | Bagchi et al. |
| 5,662,932 A | 9/1997 | Amselem |
| 5,665,277 A | 9/1997 | Johnson et al. |
| 5,665,331 A | 9/1997 | Bagchi et al. |
| 5,667,800 A | 9/1997 | De Vringer |
| 5,679,690 A | 10/1997 | Andre et al. |
| 5,683,723 A | 11/1997 | Spenlehauer et al. |
| 5,705,196 A | 1/1998 | Galan Valdivia et al. |
| 5,707,634 A | 1/1998 | Schmitt |
| 5,716,642 A | 2/1998 | Bagchi et al. |
| 5,718,919 A | 2/1998 | Ruddy |
| 5,780,062 A | 7/1998 | Frank et al. |
| 5,783,211 A | 7/1998 | Manzo et al. |
| 5,785,976 A | 7/1998 | Westesen |
| 5,834,025 A | 11/1998 | de Garavilla et al. |
| 5,843,509 A | 12/1998 | Calvo Salve et al. |
| 5,853,753 A | 12/1998 | Maierhofer et al. |
| 5,874,111 A | 2/1999 | Maitra et al. |
| 5,885,486 A | 3/1999 | Westesen |
| 5,889,051 A | 3/1999 | Chen et al. |
| 5,919,408 A | 7/1999 | Muller et al. |
| 5,932,249 A | 8/1999 | Gruber et al. |
| 5,935,939 A | 8/1999 | Kararli et al. |
| 5,952,005 A | 9/1999 | Olsson et al. |
| 5,968,551 A | 10/1999 | Oshlack |
| 6,007,845 A | 12/1999 | Domb et al. |
| 6,020,004 A | 2/2000 | Shah |
| 6,027,747 A | 2/2000 | Terracol |
| 6,083,529 A | 7/2000 | Manzo et al. |
| 6,139,870 A | 10/2000 | Verrecchia |
| 6,143,211 A | 11/2000 | Mathiowitz et al. |
| 6,146,663 A | 11/2000 | Bissery et al. |
| 6,153,225 A | 11/2000 | Lee |
| 6,177,103 B1 | 1/2001 | Pace et al. |
| 6,197,348 B1 | 3/2001 | Morella et al. |
| 6,197,349 B1 | 3/2001 | Westesen |
| 6,207,178 B1 | 3/2001 | Westesen |
| 6,217,901 B1 | 4/2001 | Perrott |
| 6,235,224 B1 | 5/2001 | Mathiowitz et al. |
| 6,245,349 B1 | 6/2001 | Yiv et al. |
| 6,254,889 B1 | 7/2001 | Kigoshi et al. |
| 6,267,985 B1 | 7/2001 | Chen |
| 6,267,989 B1 | 7/2001 | Liversidge et al. |
| 6,268,053 B1 | 7/2001 | Woiszwillo et al. |
| 6,270,806 B1 | 8/2001 | Liversidge |
| 6,280,770 B1 | 8/2001 | Pather et al. |
| 6,303,560 B1 | 10/2001 | Hartan et al. |
| 6,361,944 B1 | 3/2002 | Mirkin et al. |
| 6,375,986 B1 | 4/2002 | Ryde |
| 6,383,500 B1 | 5/2002 | Wooley et al. |
| 6,391,338 B1 | 5/2002 | Frisbee et al. |
| 6,406,745 B1 | 6/2002 | Talton |
| 6,428,814 B1 | 8/2002 | Bosch et al. |
| 6,440,458 B1 | 8/2002 | Yamashita et al. |
| 6,443,898 B1 | 9/2002 | Unger et al. |
| 6,447,806 B1 | 9/2002 | Gassmann |
| 6,458,383 B2 | 10/2002 | Chen et al. |
| 6,462,093 B1 | 10/2002 | Miyamoto |
| 6,479,146 B1 | 11/2002 | Caruso et al. |
| 6,485,743 B1 | 11/2002 | Jung et al. |
| 6,509,034 B1 | 1/2003 | Calanchi et al. |
| 6,517,859 B1 | 2/2003 | Tice et al. |
| 6,537,579 B1 | 3/2003 | Desai et al. |
| 6,544,497 B2 | 4/2003 | Zhu et al. |
| 6,548,264 B1 | 4/2003 | Tan et al. |
| 6,551,619 B1 | 4/2003 | Penkler et al. |
| 6,555,139 B2 | 4/2003 | Sharma |
| 6,565,873 B1 | 5/2003 | Shefer |
| 6,565,875 B2 | 5/2003 | Tice et al. |
| 6,565,885 B1 | 5/2003 | Tarara et al. |
| 6,576,264 B1 | 6/2003 | Henriksen et al. |
| 6,579,519 B2 | 6/2003 | Maitra et al. |
| 6,592,899 B2 | 7/2003 | Fowers et al. |
| 6,592,901 B2 | 7/2003 | Durig et al. |
| 6,592,903 B2 | 7/2003 | Ryde |
| 6,596,262 B2 | 7/2003 | Zhu et al. |
| 6,596,311 B1 | 7/2003 | Dobetti |
| 6,607,784 B2 | 8/2003 | Kipp et al. |
| 6,616,869 B2 | 9/2003 | Mathiowitz et al. |
| 6,620,351 B2 | 9/2003 | Gupta |
| 6,623,761 B2 | 9/2003 | Hassan |
| 6,632,671 B2 | 10/2003 | Unger |
| 6,638,537 B2 | 10/2003 | Dennis et al. |
| 6,638,621 B2 | 10/2003 | Anderson |
| 6,638,994 B2 | 10/2003 | Crooks et al. |
| 6,645,517 B2 | 11/2003 | West et al. |
| 6,645,569 B2 | 11/2003 | Cramer et al. |
| 6,649,192 B2 | 11/2003 | Alonso Fernandez et al. |
| 6,652,967 B2 | 11/2003 | Yadav et al. |
| 6,656,504 B1 | 12/2003 | Bosch et al. |
| 6,656,507 B2 | 12/2003 | Petereit et al. |
| 6,656,984 B1 | 12/2003 | Haasmaa et al. |
| 6,660,382 B2 | 12/2003 | Nouri et al. |
| 6,663,885 B1 | 12/2003 | Hager et al. |
| 6,669,959 B1 | 12/2003 | Adjei et al. |
| 6,677,386 B1 | 1/2004 | Giezen et al. |
| 6,682,761 B2 | 1/2004 | Pace |
| 6,682,895 B2 | 1/2004 | Mirkin et al. |
| 6,685,960 B1 | 2/2004 | Gasco |
| 6,692,769 B1 | 2/2004 | Ishibashi et al. |
| 6,696,084 B2 | 2/2004 | Pace et al. |
| 6,709,622 B2 | 3/2004 | Billiet |
| 6,720,008 B2 | 4/2004 | Allison |
| 6,726,934 B1 | 4/2004 | Prokop |
| 6,746,635 B2 | 6/2004 | Mathiowitz et al. |
| 6,755,915 B1 | 6/2004 | Van Soest et al. |
| 6,756,062 B2 | 6/2004 | Johnston et al. |
| 6,761,903 B2 | 7/2004 | Chen et al. |
| 6,780,324 B2 | 8/2004 | Le Garrec et al. |
| 6,793,938 B2 | 9/2004 | Sankaram |
| 6,824,791 B2 | 11/2004 | Mathiowitz et al. |
| 6,827,946 B2 | 12/2004 | Hirsh |
| 6,863,914 B1 | 3/2005 | Auweter et al. |
| 6,869,617 B2 | 3/2005 | Kipp et al. |
| 6,878,693 B2 | 4/2005 | Goldshtein |
| 6,887,493 B2 | 5/2005 | Shefer |

(56) References Cited

U.S. PATENT DOCUMENTS

| | | | |
|---|---|---|---|
| 6,890,512 B2 | 5/2005 | Roser et al. | |
| 7,081,450 B2 | 7/2006 | Goldshtein | |
| 7,105,176 B2 | 9/2006 | Auweter et al. | |
| 2002/0012675 A1 | 1/2002 | Jain et al. | |
| 2002/0054914 A1 | 5/2002 | Morcol | |
| 2002/0068092 A1 | 6/2002 | Bosch et al. | |
| 2002/0081334 A1 | 6/2002 | Johnston et al. | |
| 2002/0106403 A1 | 8/2002 | Parikh et al. | |
| 2002/0127278 A1 | 9/2002 | Kipp et al. | |
| 2002/0142017 A1 | 10/2002 | Simonnet | |
| 2002/0169274 A1* | 11/2002 | Eisenberg et al. | 528/354 |
| 2003/0003155 A1 | 1/2003 | Kipp et al. | |
| 2003/0026844 A1 | 2/2003 | Lee et al. | |
| 2003/0031719 A1 | 2/2003 | Kipp et al. | |
| 2003/0049323 A1 | 3/2003 | Hitt et al. | |
| 2003/0095928 A1 | 5/2003 | McGurk et al. | |
| 2003/0129239 A1 | 7/2003 | Goldshtein | |
| 2003/0147965 A1 | 8/2003 | Bassett et al. | |
| 2003/0166509 A1 | 9/2003 | Edwards et al. | |
| 2003/0170309 A1 | 9/2003 | Babcock et al. | |
| 2003/0190347 A1 | 10/2003 | Supersaxo et al. | |
| 2003/0206949 A1 | 11/2003 | Parikh et al. | |
| 2003/0235619 A1 | 12/2003 | Allen et al. | |
| 2004/0009229 A1 | 1/2004 | Unger et al. | |
| 2004/0013613 A1 | 1/2004 | Jain et al. | |
| 2004/0018229 A1 | 1/2004 | Henriksen et al. | |
| 2004/0018236 A1 | 1/2004 | Gurny et al. | |
| 2004/0047913 A1 | 3/2004 | Allemann et al. | |
| 2004/0067251 A1 | 4/2004 | Johnston et al. | |
| 2004/0071776 A1 | 4/2004 | Boudy et al. | |
| 2004/0091546 A1 | 5/2004 | Johnson | |
| 2004/0180005 A1 | 9/2004 | Jurgens | |
| 2004/0191319 A1 | 9/2004 | Yun | |
| 2004/0220081 A1 | 11/2004 | Kreitz et al. | |
| 2004/0245662 A1 | 12/2004 | Chaubal et al. | |
| 2004/0247624 A1 | 12/2004 | Unger et al. | |
| 2005/0013866 A1 | 1/2005 | Maincent et al. | |
| 2005/0238716 A1 | 10/2005 | Verrijk et al. | |
| 2006/0134220 A1 | 6/2006 | Aboubakar et al. | |

OTHER PUBLICATIONS

Shuai X et al, "Micellar carriers based on block copolymers of poly(epsilon-caprolactone) and poly(ethylene glycol) for doxorubicin delivery," Journal of Controlled Release, vol. 98, No. 3, pp. 415-426, 2004.

Aliabadi H M et al, "Micelles of methoxy poly(ethylene oxide)-b-poly(@?-caprolactone) as vehicles for the solubilization and controlled delivery of cyclosporine A," Journal of Controlled Release, vol. 104, No. 2, pp. 301-311, 2005.

Hsieh Ming-Fa et al, "Nano-sized micelles of block copolymers of methoxy poly(ethylene glycol)-poly(epsilon-caprolactone)-graft-2-hydroxyethyl cellulose for doxorubicin delivery," Journal of Nanoscience and Nanotechnology, vol. 8, No. 5, pp. 2362-2368, 2008.

Al-Kassas, R., "Design and In Vitro Evaluation of Gentamicin-Eudragit Microspheres Intended for Intra-Ocular Administration," Journal of Microencapsulation, 21:1(2004)71-81.

Amrite, A.C., S.P. Ayalasomayajula, and U. Kompella, "Ocular Distribution of Intact Nano- and Micro Particles Following Subconjunctival and Systemic Routes of Administration," Drug Delivery Techn., vol. 2, No. 3, 2003.

Barbu, E., L. Verestiuc, T.G. Nevell, and J. Tsibouldis, "Polymeric Materials for Ophthalmic Drug Delivery: Trends and Perspectives," J. of Materials Chemistry, 16(2006)3439-3443.

Bodmeier et al., "Preparation and Evaluation of Drug-Containing Polymeric Nanosuspensions," presented at the 5th International Conference on Pharmaceutical Technology, Paris, France, 1989. Proceedings vol. 2, pp. 265-268.

Bodmeier, et al., "Indomethacin Polymer Nanosuspension Prepared by Microfluidization", Journal of Controlled Release, 12 (1990) 223-233.

Bourges, J.-L., S.E. Gautier, F. Delie, R.A. Bejjani, J.-C. Jeanny, R. Gurny, D. BenEzra, and F.F. Behar-Cohen, "Ocular Drug Delivery Targeting the Regina and Retinal Pigment Epithelium Using Polylactide Nanoparticles," Investigative Ophthalmology and Visual Science, 44:8(2003)3562-3569.

Briancon, S., H. fessi, F. Lecomet, and J. Lieto, "Study and Scale-Up of a Nanoprecipitation Process," Industrial Crystallization 1999 (IChemE), pp. 1-10.

Bucolo, C., A. Maltese, F. Maugeri, B. Busa, G. Puglisi, and R. Pignatello, "Eudragit RL100 Nanoparticle System for the Ophthalmic Delivery of Cloricromene," Journal of Pharmacy and Pharmacology, 56(2004)841 846.

Calvo, P., J.L. Vila-Jato, and M.J. Alonso, "Evaluation of Cationic Polymer-Coated Nanocapsules as Ocular Drug Carriers," International Journal of Pharmaceutics, 153(1997)41-50.

Carrasquillo, K.G., J.A. Ricker, I.K. Rigas, J.W. Miller, E.S. Gragoudas, and A.P. Adamis, "Controlled Delivery of the Anti-VEGF Aptamer EYE001 with Poly(lactic-co-glycolic) Acid Microspheres," Investigative Ophthalmology and Visual Science, 44:1(2003)290-299.

Cavalli, R., M.R. Gasco, P. Chetoni, S. Burgalassi, and M.F. Saettone, "Solid Lipid Nanoparticles (SLN) as Ocular Delivery System for Tobramycin," International J. Pharmaceutics, 238(2002)241-245.

Chen et al., "Comparison of Albumin and Casein Microspheres as a Carrier for Doxorubicin," J. Pharm. Pharmacol.39(1987)978-985.

Chiou, W.L., and S.Riegelman, J. Pharm. Sci., 60:9(1971)1281-1302.

Couvreur, Microspheres and Drug Therapy, Elsevier, (1984) pp. 103-115.

De, T.K., D.J. Rodman, B.A. Holm, P.N. Prasad, and E.J. Bergey, "Brimonidine Formulation in Polyacrylic Acid Nanoparticles for Ophthalmic Delivery," J. Microencapsualtion, 20:3)2003)361-374.

Decampos, A.M., A. Sanchez, and M.J. Alonso, "Chitosan Nanoparticles: A New Vehicle for the Improvement of the Delivery of Drugs to the Ocular Surface. Application to Cyclosporin A," International J. of Pharmaceutics, 224(2001)159-168.

Decampos., A.M., A. Sanchez, R. Gref, P. Calvo, and M.J. Alonso, "The Effect of a PGE Versus a Chitosan Coating on the Interaction of Drug Colloidal Carriers with the Ocular Mucosa," European Journal of Pharmaceutical Sciences, 20(2003)73-81.

Dejaeghere, F., E. Allemann, J.-C. Leroux, W. Stevels, J. Feijen, E. Doelker, and R. Gurny, "Formulation of Lyoprotection of Poly(Lactic Acid-Co-Ethylene Oxide) Nanoparticles: Influence on Physical Stability and in Vitro cell Uptake," Pharmaceutical Research, 16:6(1999)859-866.

Desai, S.D., and J. Blanchard, "Pluronic F127-Based Ocular Delivery System Containing Biodegradable Polyisobutylcyanoacrylate Nanocapsules of Pilocarpine," Drug Delivery, 7(2000)201-207.

Fee, C.A., and R.I. Pettigrew, "National Institute of Biomedical Imaging and Bioengineering: Poised for the Future," National Institute of Biomedical Imaging and Bioengineering, 229:3(2003)636-637.

Fessi, H., F. Puisieux, J.Ph. Devissaguet, N. Ammoury, and S. Benita, "Nanocapsule Formation by Interfacial Polymer Deposition Following Solvent Displacement," International J. of Pharmaceutics, 55(1989)R1-R4.

Ford, J.L., Pharm. Acta Helv., 61:3(1986)69-87.

Fox et al., from Proteins in Food Processing, R.Y. Yada (ed), CRC Press, 2004, Chapter 3: The Caseins pp. 29-71.

Gavini, E., P. Chetoni, M. Cossu, M.G. Alvarez, M.F. Saettone, and P. Giunchedi, "PLGA Microspheres for the Ocular Delivery of a Peptide Drug, Vancomycin Using Emulsification/Spray-Drying as the Preparation Method: In Vitro/In Vivo Studies," European Journal of Pharmaceutics and Biopharmaceutics, 57(2004)207-212.

Giannavola, C., C. Bucolo, A. Maltese, D. Paolino, M.A. Vandelli, G. Puglisi, V.H.L. Lee, and M. Fresta, "Influence of Preparation Conditions on Acyclovir-Loaded Poly-d,l-Lactic Acid Nanospheres and Effect of PEG Coating on Ocular Drug Bioavailability." Pharmaceutical Research, 20:4(2003)584-590.

Gurny, Drug Develop. Ind. Pharm. 7(1), 1-25, 1981.

Gurny, R., T. Boye, and H. Ibrahim, "Ocular Therapy with Nanoparticulate Systems for Controlled Drug Delivery," Journal of Controlled Release, 2(1985)353-361.

(56) References Cited

OTHER PUBLICATIONS

Harmia, J. Microencapsulation, 1986 vol. 3, No. 1, p. 3-12.
Hasegawa, H., et al., Chem. Pharm. Bull., 33:4(1985)1615-1619; Chem. Pharm. Bull., 34:5(1986)2183-2190; Chem. Pharm. Bull., 36:12(1988) 4941-4950.
Herrero-Vanrell, R., and M.F. Refojo, "Biodegradable Microspheres for Vitreoretinal Drug Delivery," Advanced Drug Delivery Reviews, 52(2001)5 16.
Hornig et al., "Novel Nanoparticles Based on Dextran Esters with Unsaturated Moieties," Macromolecular Rapid Commun., 2005, 26, 1908-1912.
Hornig et al., "Structure Design of Multifunctional Furoate and Pyroglutamate Esters of Dextran by Polymer-Analogous Reactions," Macromol. Biosci. 2007, 7, 297-306.
Hsiue, G.-H., S.-H. Hsu, C.-C. Yang, S.-H. Lee,a nd I.-K. Yang, "Preparation of Controlled Release Ophthalmic Drops, for Glaucoma Therapy Using Thermosensitive poly-N-Isopropylacrylamide," Biomaterials, 23(2002)457 462.
Kim, S., Y.T. Lim, E.G. Soltesz, A.M. DeGrand, J. Lee, A. Nakayama, J.A. Parker, T. Mihaljevic, R.G. Laurence, D.M. Dor, L.H. Cohn, M.G. Bawendi, and J.V. Frangioni,"Near-Infrared Fluorescent Type II Quantum Dots for Sentinel Lymph Node Mapping," Nature Biotechnology, 22:1(2004)93-97.
Knepp et al., Synthesis, Properties, and Intratumoral Evaluation of Mitoxantrone-Loaded Casein Microspheres in Lewis Lung Carcinoma, J. Pharm. Pharmacol., 45(1993)887-891.
Kompella, U.B., N. Bandi, and S.P. Ayalasomayajula, "Subconjunctival Nano- and Microparticles Sustain Retinal Delivery of Budesonide, A Corticosteroid Capable of Inhibiting VEGF Expression," Investigative Ophthalmology and Visual Science, 44:3(2003)1192-1201.
Kumar, M.M.V., "Nano and Microparticles as Controlled Drug Delivery devices," J. Pharm. Pharmaceutical Sciences, 3:2(2000)234-258.
Latha et al., Casein as a Carrier Matrix for 5-Fluorouracil: Drug Release from Microspheres, Drug-Protein Conjugates and In-Vivo Degradation of Microspheres in Rat Muscle, J. Pharm. Pharmacol., 46(1994)858-862.
Latha et al., Glutaraldehyde Cross-Linked Bovine Casein Microspheres as a Matrix for the Controlled Release of Theophylline: In Vitro Studies, J. Pharm. Pharmacol., 46(1994)8-13.
Latha et al., Progesterone Release from Glutaraldehyde Cross-Linked Casein Microspheres: In Vitro Studies and In Vivo Response in Rabbits, Contraception, 61(2000)329-334.
Lecorre, P., J.H. Rytting, V. Gajan, F. Chevanne, and R. LeVerge, "In Vitro Controlled Release Kinetics of Local Anaesthetics from Poly(D,L-lactice) and Poly (lactice-co-glycolide) Microspheres," Journal of Microencapsulation, 1997, pp. 243-255.
Lellemand, F., O. Felt-Baeyens, K. Besseghir, F. Behar-Cohen, and R. Gurny, "Cyclosporine A Delivery to the Eye: A Pharmaceutical Challenge," European J. of Pharmaceutics and Biopharmaceutics, 56(2003)307 318.
Lemarchand, C., R. Gref, and P. Couvreur, "Polysaccharide-Decorated Nanoparticles," European J. of Pharmaceutics and Biopharmaceutics, 58(204,327-341, 2004.
Lemarchand, et al., "Influence of polysaccharide coating on the interactions of nanoparticles with biological systems," Biomaterials, 27(2006)108-118.
Liebert, et al., "Nanoparticles on the Basis of Highly Functionalized Dextrans," J. Am. Chem. Soc. 2005, 127, 10484-10485.
Longmuir, K.J., R.T. Robertson, S.M. Haynes, J.L. Baratta, and A.J. Waring, "Effective Targeting of Liposomes to Liver and Hepatocytes In Vivo by Incorporation of a Plasmodium Amino Acid Sequence," Pharmaceutical Research, 23:4(2006)759-769.
Losa, C., L. Marchal-Heussler, F. Orallo, J.L. Vila Jato, and M.J. Alonso, "Design of New Formulations for Topical Ocular Administration: Polymeric Nanocapsules Containing Metipranolol," Pharmaceutical Research, 10:1(1993)80-87.
Merodio, M., J.M. Irache, F. Valamanesch, and M. Mirshahi, "Ocular Disposition and Tolerance of Ganciclovir-Loaded Albumin Nanoparticles after Intravitreal Injection in Rats," Biomaterials, 23(2002)1587-1594.
Mirshahi et al., Development of Drug Delivery Systems from Vegetal Proteins: Legumin Nanoparticles, Drug Dev. Indust.Pharm., 22:8(1996)841-846.
Mora-Gutierrez et al., Modeling Calcium-Induced Solubility in Caprine Milk Caseins Using a Thermodynamic Linkage Approach, J. Dairy Sci., 76(1993)3698-3710.
Ohio State FST 822 Class Lecture, Casein, 2006, 5 pp.
Pignatello, R., C. Bucolo, and G. Puglisi, "Ocular Tolerability of Eudragit RS100 and RL100 Nanosuspensions as Carriers for Ophthalmic Controlled Drug Delivery," Journal of Pharmaceutical Sciences, 91:12(2002)2636-2641.
Pignatello, R., C. Bucolo, G. Spedalieri, A. Maltese, and G. Puglisi, "Flurbiprofen-Loaded Acrylate Polymer Nanosuspensions for Ophthalmic Application," Biomaterials, 23(2002)3247-3255.
Pignatello, R., C. Bucolo, P. Ferra, A. Maltese, A. Puleo, and G. Puglisi, "Eudragit RS100 Nanosuspensions for the Ophthalmic Controlled Delivery of Ibuprofen," European Journal of Pharmaceutical Sciences, 16(2002)53 61.
Qaddoumi, M.G., H. Ueda, J. Yang, J. Davda, V. Labhasetwar, and V.H.L. Lee, "The Characteristics and Mechanisms of Uptake of PLGA Nanoparticles in Rabbit Conjuctival Epithelial Cell Layers," Pharmaceutical Research, 21:4(2004)641-648.
Raveendran, P, J. Fu, and S.L. Wallen, "Completely 'Green' Synthesis and Stabilization of Metal Nanoparticles," J. American Chemical Society, 125(2003)13940-13941.
Santinho et al., Influence of Formulation on the Physiochemical Properties of Casein Microparticles, Int'l J. Pharm., 186(1999)191-198.
Scholes, P.D., A.G.A. Coombes, L. Ilium, S.S. Savis, M. Vert, and M.C. Davies, "The Preparation of Sub-200 nm Poly(lactide-co-glycolide) Microspheres for Site-Specific Drug Delivery," J. Controlled Release, 25(1993)145-153.
Sjostrom, et al., Journal of Pharmaceutical Sciences, vol. 82, No. 6 Jun. 1993, pp. 584-589.
Sugimoto, I., K. Sasaki, A. Kuchiki, T. Ishihara, and H. Nakagawa, Chem. Pharm. Bull, 30:12(1982)4479-4488.
Suverkrup, R., S. Grunthal, O. Krasichkova, S. Maier, A. Weischselbaum, B. Neff, M. Diestelhorst, S. Dinslage, and A. Lux, "The Ophthalmic Lyophilisate Carrier System (OLCS): Development of a Novel Dosage Form, Freeze-Drying Technique, and In Vitro Quality Control Tests,"European J. Pharmaceutics and Biopharmaceutics, 57(2004)269-277.
Takayama, K., N. Nambu, and T. Nagai., Chem. Pharm. Bull., 30:2(1982)673-678.
Takenaka, H., Y. Kawashima and S.Y. Lin, J. Pharm. Sci., 69:12(1980)1388-1392.
Takeuchi, H., T. Handa and Y. Kawashima, Chem. Pharm. Bull., 35:9(1987)3800-3806.
Tuovinen, L., E. Ruhanen, T. Kinnarinen, S. Ronkko, J. Pelkonen, A. Urtti, S. Peltonen, and K. Jarvinen, "Starch Acetate Microparticles for Drug Delivery Into Retinal Pigment Epithelium—In Vitro Study," J. of Controlled Release, 98(2004)407-413.
Ueda, M., A. Iwara, and J. Kreuter, "Influence of the Preparation Methods on the Drug Release Behaviour of Loperamide-Loaded Nanoparticles," J. Microencapsulation, 15:3(1998)361-372.
University of Guelph, Dairy Chemistry and Physics, 2006, 16 pp.
Vandamme, Th.F., "Microemulsions as Ocular Drug Delivery Systems: Recent Developments and Future Challenges," Progress in Retinal and Eye Research, 21(2002)15-34.
Vandervoort, J., and A. Ludwig, "Preparation and Evaluation of Drug-Loaded Gelatin Nanoparticles for Topical Ophthalmic Use," European J. of Pharmaceutics and Biopharmaceutics, 57(2004)251-261.
Willmott et al., Doxorubicin-Loaded Casein Microspheres: Protean Nature of Drug Incorporation J. Pharm. Pharmacol. 42(1992)472-475.
Zahr, A.S., M. de Villiers, and M.V. Pishko, "Encapsulation of Drug Nanoparticles in Self-Assembled Macromolecular Nanoshells," Langmuir, 21(2005)503 410.
Zimmer, A., and J. Kreuter, "Microspheres and Nanoparticles Used in Ocular Delivery Systems," Advanced Drug Delivery Reviews, 16(1995)61-73.

* cited by examiner

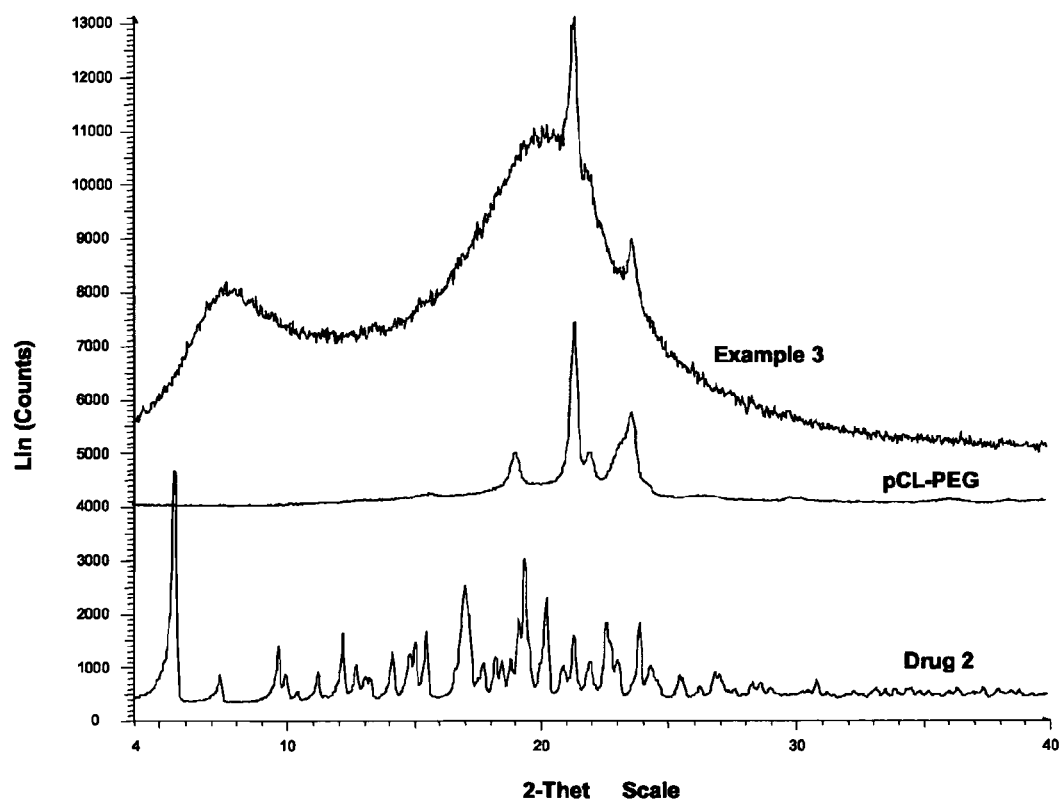

NANOPARTICLES COMPRISING A NON-IONIZABLE CELLULOSIC POLYMER AND AN AMPHIPHILIC NON-IONIZABLE BLOCK COPOLYMER

This is a 371 of PCT/IB/2008/001352 filed May 26, 2008, and claims priority of U.S. 60/941,755 filed Jun. 4, 2007.

BACKGROUND OF THE INVENTION

The present invention relates to nanoparticles comprising a poorly water-soluble drug, a poorly aqueous soluble non-ionizable cellulosic polymer having an ether- or ester-linked alkyl substituent, and a poorly aqueous soluble polymeric amphiphilic non-ionizable block copolymer having a hydrophobic block that is a polylactone and a hydrophilic block that is polyethylene oxide or polyethylene glycol.

It is known that poorly water-soluble drugs may be formulated as nanoparticles. Nanoparticles are of interest for a variety of reasons, such as to improve the bioavailability of poorly water-soluble drugs, to provide targeted drug delivery to specific areas of the body, to reduce side effects, or to reduce pharmacokinetic variability in vivo.

A variety of approaches have been taken to formulate drugs as nanoparticles. One approach is to decrease the size of crystalline drug by grinding or milling the drug in the presence of a surface modifier. See, e.g., U.S. Pat. No. 5,145,684. Another approach to forming nanoparticles is to precipitate the drug in the presence of a film forming material such as a polymer. See, e.g., U.S. Pat. No. 5,118,528.

Nanoparticles containing a drug and a non-ionizable polymer are known in the art. Bodmeier and Chen (*J. Controlled Release*, 12, (1990) 223-233) describe nanoparticles prepared from ethylcellulose and a variety of aqueous soluble surfactants, as well as mixtures of ethylcellulose and poly(methyl methacrylate). U.S. Pat. No. 5,919,408 discloses nanoparticles prepared from ethylcellulose and the aqueous soluble surfactants sodium dodecyl sulphate and a polyoxyethylene-polyoxypropylene copolymer. U.S. Pat. No. 5,118,528 discloses nanoparticles prepared from poly(lactic acid) and a polyoxyethylene-polyoxypropylene copolymer. U.S. Pat. No. 5,543,158 discloses nanoparticles prepared from blends of poly(lactide-co-glycolide) and poly(lactide-co-glycolide-b-ethylene glycol). EP 1 180 062 B1 discloses nanoparticles prepared from blends of poly(lactic acid) and a polyoxyethylene-polyoxypropylene copolymer.

While these methods of forming nanoparticles are functional, nevertheless there remain a number of problems associated with the use of nanoparticles to deliver pharmaceutical compounds to the body. First, it is difficult to form very small particles. Second, once particles of the target size are formed, they must remain stable over time in a variety of different environments. Often, the nanoparticles are formed in a liquid environment. The nanoparticles must be stabilized so that they do not aggregate in solution into larger particles. In addition, the drug in the nanoparticles must be stabilized so that it does not crystallize in the use environment.

Third, the nanoparticles must be well tolerated in the body. Often surface modifiers such as surfactants are used to stabilize the nanoparticles, but such materials can have adverse physiological effects when administered in vivo. In addition, such materials are often labile, dissolving into the aqueous use environment, resulting in undesirable agglomeration of nanoparticles. Ionizable stabilizers are often not ionized in the low pH of a gastric environment, resulting in agglomeration of the nanoparticles in the stomach. Additionally, without a surface modifier present, the surface of the nanoparticles is unprotected, leading to a decrease in performance and stability.

Finally, the nanoparticles must be formulated to provide optimum delivery. The nanoparticles should provide good bioavailability of the poorly water-soluble drug. In some applications, it is desired that the nanoparticles provide reduced differences in exposure when administered orally to subjects in the fed state versus in the fasted state. Alternatively, it may be desired to provide controlled or sustained release of the drug below pre-determined dissolved drug concentrations in vivo. It may be desired to administer the nanoparticles through non-oral routes, such as by parenteral, topical, or ocular delivery.

Accordingly, there is still a continuing need for nanoparticles that are stable, in the sense of not forming crystalline drug over time or aggregating into larger particles, and that improve the bioavailability of low-solubility drugs.

BRIEF SUMMARY OF THE INVENTION

In a first aspect, a pharmaceutical composition comprises nanoparticles, the nanoparticles comprising: (a) a poorly water-soluble drug having a solubility in water of less than 5 mg/mL over the pH range of 6.5 to 7.5 at 25° C., at least 90 wt % of the drug in the nanoparticles being non-crystalline; (b) a poorly aqueous soluble non-ionizable cellulosic polymer having an ether- or ester-linked alkyl substituent; and (c) a poorly aqueous soluble polymeric amphiphilic non-ionizable block copolymer having a hydrophobic block that is a polylactone, and a hydrophilic block that is polyethylene oxide or polyethylene glycol; wherein the nanoparticles have an average size of less than 500 nm; the nanoparticles comprising from 1 wt % to 80 wt % drug, from 10 wt % to 75 wt % non-ionizable cellulosic polymer, and from 5 wt % to 60 wt % amphiphilic non-ionizable stabilizer; and the drug, the non-ionizable cellulosic polymer, and the amphiphilic non-ionizable block copolymer collectively constitute at least 60 wt % of the nanoparticles.

In one embodiment, the non-ionizable cellulosic polymer is selected from the group consisting of ethylcellulose, cellulose acetate, cellulose propionate, cellulose butyrate, cellulose acetate butyrate, and mixtures thereof.

In another embodiment, the amphiphilic non-ionizable block copolymer is poly(ethylene oxide-co-ε-caprolactone).

In yet another embodiment, the non-ionizable cellulosic polymer is ethyl cellulose and the amphiphilic non-ionizable block copolymer is poly(ethylene oxide-co-ε-caprolactone).

The inventors have found that nanoparticles comprising a poorly water-soluble drug, a poorly aqueous soluble non-ionizable cellulosic polymer, and a poorly aqueous soluble polymeric amphiphilic non-ionizable block copolymer result in a material that improves the bioavailability of the drug when administered to an aqueous use environment.

Because the nanoparticles are formed from a blend of a poorly aqueous soluble non-ionizable cellulosic polymer and an amphiphilic non-ionizable block copolymer, the stability of the non-crystalline drug and the suspension stability of the nanoparticle can be addressed independently, resulting in nanoparticles with improved performance and stability.

First, the poorly aqueous soluble non-ionizable cellulosic polymer used in the nanoparticles stabilizes the poorly water soluble drug in the sense of reducing the rate of crystallization of the drug in the solid state and while in suspension in vivo. The non-ionizable cellulosic polymer is chosen so that a portion of the drug is soluble in the polymer. This helps prevent or reduce the rate of crystallization of the non-crystalline drug in the nanoparticle. In addition, because the non-ionizable cellulosic polymer is poorly aqueous soluble at physiological pH, the nanoparticles maintain the drug within a solid (or at least undissolved) polymer matrix when the nanoparticles are suspended in an aqueous solution, further preventing or reducing crystallization of the drug. It is well known that the non-crystalline form of a low-solubility drug provides a greater aqueous concentration of drug relative to the crystalline form of the drug when administered to an aqueous use environment. However, it is also well known that when the drug is not stabilized in the non-crystalline form, the drug rapidly converts to the crystalline form in the use environment. See, for example, Hancock and Parks (*Pharmaceutical Research, Vol.* 17, No. 4, 2000). Thus, the poorly aqueous soluble non-ionizable cellulosic polymer is selected to maintain the stability of the non-crystalline drug in the nanoparticle and while suspended in an aqueous solution, resulting in an enhanced concentration of free drug when the nanoparticle is administered to an aqueous use environment.

Second, the poorly aqueous soluble polymeric amphiphilic non-ionizable block copolymer may be chosen to provide stability to the nanoparticles. The block copolymer is selected such that it reduces or eliminates agglomeration of the nanoparticles when in an aqueous suspension. In addition, nanoparticles made using an amphiphilic non-ionizable block copolymer may have improved re-suspendability relative to nanoparticles made using surfactants.

Finally, nanoparticles formed using a poorly aqueous soluble polymeric amphiphilic non-ionizable stabilizer may provide improved toleration relative to conventional nanoparticles that incorporate a substantial amount of surfactant to stabilize the nanoparticles.

The combination of the two different materials—the poorly aqueous soluble non-ionizable cellulosic polymer and the amphiphilic non-ionizable block copolymer—provides a synergistic effect that cannot be obtained when using only one material, resulting in improved stability and re-suspendability of the nanoparticles.

The foregoing and other objectives, features, and advantages of the invention will be more readily understood upon consideration of the following detailed description of the invention.

BRIEF DESCRIPTION OF THE SEVERAL VIEWS OF THE DRAWINGS

FIG. 1 is a powder X ray diffraction (PXRD) diffractogram of the solid nanoparticles of Example 3.

DETAILED DESCRIPTION OF THE INVENTION

The nanoparticles of the present invention comprise a poorly water-soluble drug, a poorly aqueous soluble non-ionizable cellulosic polymer, and a poorly aqueous soluble polymeric amphiphilic non-ionizable block copolymer. At least 90 wt % of the drug in the nanoparticle is non-crystalline. The nature of the nanoparticles, suitable cellulosic polymers, block copolymers, drugs, and methods for making nanoparticles are described in detail below.

Nanoparticles

The nanoparticles are small particles comprising the drug, the poorly aqueous soluble non-ionizable cellulosic polymer, and the amphiphilic non-ionizable block copolymer. By "nanoparticles" is meant a plurality of small particles in which the average size of the particles is less than about 500 nm. In suspension, by "average size" is meant the effective cumulant diameter as measured by dynamic light scattering (DLS), using for example, Brookhaven Instruments' 90Plus particle sizing instrument. By "size" is meant the diameter if the particles were spherical particles, or the maximum diameter for non-spherical particles. Preferably, the average size of the nanoparticles is less than 400 nm, more preferably less 300 nm, more preferably less than 200 nm, more preferably less than 150 nm, and most preferably less than 100 nm.

The width of the particle size distribution in suspension is given by the "polydispersity" of the particles, Which is defined as the relative variance in the correlation decay rate distribution, as is known by one skilled in the art. See B. J. Fisken, "Revisiting the method of cumulants for the analysis of dynamic light-scattering data," *Applied Optics,* 40(24), 4087-4091 (2001) for a discussion of cumulant diameter and polydispersity. Preferably, the polydispersity of the nanoparticles is less than 0.5. More preferably, the polydispersity of the nanoparticles is less than about 0.3. In one embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 200 nm with a polydispersity of 0.5 or less. In yet another embodiment, the average size of the nanoparticles is less than 200 nm with a polydispersity of 0.3 or less.

At least 90 wt % of the drug in the nanoparticles is non-crystalline. The term "crystalline," as used herein, means a particular solid form of a compound that exhibits long-range order in three dimensions. "Non-crystalline" refers to material that does not have long-range three-dimensional order, and is intended to include not only material which has essentially no order, but also material which may have some small degree of order, but the order is in less than three dimensions and/or is only over short distances. Another term for a non-crystalline form of a material is the "amorphous" form of the material. As previously discussed, the non-crystalline form of a low-solubility drug is preferred as it provides a greater aqueous concentration of drug relative to the crystalline form of the drug in an aqueous use environment. Preferably at least about 95 wt % of the drug in the nanoparticle is non-crystalline; in other words, the amount of drug in crystalline form does not exceed about 5 wt %. Amounts of crystalline drug may be measured by Powder X-Ray Diffraction (PXRD), by Differential Scanning Calorimetry (DSC), by solid state nuclear magnetic resonance (NMR), or by any other known quantitative measurement.

The nanoparticles can exist in a number of different configurations. In one embodiment, the nanoparticles comprise a core, the core comprising the non-crystalline drug and the poorly aqueous soluble non-ionizable cellulosic polymer. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, Fourier transform infra red (FTIR) analysis, and Raman spectroscopy; (3) chromatographic techniques, such as high performance liquid chromatography (HPLC), and gel-permeation chromatography (GPC); and (4) other techniques known in the art.

In one embodiment, the non-crystalline drug and the poorly aqueous soluble non-ionizable cellulosic polymer constitute at least 60 wt % of the core, more preferably at least 80 wt % of the core. In another embodiment, the core consists essentially of the non-crystalline drug and the poorly aqueous soluble non-ionizable cellulosic polymer.

The non-crystalline drug present in the core can exist in non-crystalline pure drug domains, as a thermodynamically stable solid solution of non-crystalline drug homogeneously distributed throughout the non-ionizable cellulosic polymer, as a supersaturated solid solution of non-crystalline drug homogeneously distributed throughout the non-ionizable cellulosic polymer, or any combination of these states or those states that lie between them. When the glass-transition temperature ($T_g$) of the non-crystalline drug is different from the $T_g$ of the pure polymer by at least about 20° C., the core may exhibit a $T_g$ that is different from the $T_g$ of pure non-crystalline drug or pure polymer. Preferably, less than 20 wt % of the drug is present in non-crystalline drug domains, with the remaining drug homogeneously distributed throughout the non-ionizable cellulosic polymer.

In yet another embodiment, the core comprises the non-crystalline drug, the poorly aqueous soluble non-ionizable cellulosic polymer, and the amphiphilic non-ionizable block copolymer. In this embodiment, the drug, non-ionizable cellulosic polymer, and the amphiphilic non-ionizable block copolymer constitute at least 60 wt % of the core, more preferably at least 80 wt % of the core.

The core may be (1) a homogeneous molecular mixture of drug, non-ionizable cellulosic polymer, and the amphiphilic non-ionizable block copolymer, (2) domains of pure drug, domains of pure non-ionizable cellulosic polymer, and domains of pure amphiphilic non-ionizable block copolymer distributed throughout the core, or (3) any combination of these states or those states that lie between them. In one embodiment, the drug, non-ionizable cellulosic polymer, and amphiphilic non-ionizable block copolymer are homogeneously distributed throughout the core as a supersaturated solid solution. In another embodiment, the surface portion of the nanoparticle has a higher concentration of amphiphilic non-ionizable block copolymer relative to the nanoparticle as a whole.

In still another embodiment, the core comprises the non-crystalline drug and the poorly aqueous soluble non-ionizable cellulosic polymer, with the amphiphilic non-ionizable block copolymer adsorbed to the surface portion of the nanoparticle.

In yet another embodiment, the core comprises the non-crystalline drug, the poorly aqueous soluble non-ionizable cellulosic polymer, and a portion of the amphiphilic non-ionizable block copolymer. The remaining portion of the amphiphilic non-ionizable block copolymer is adsorbed to the surface portion of the nanoparticle. In this embodiment, a portion of the amphiphilic non-ionizable block copolymer is integral to the core, while the remaining portion of the amphiphilic non-ionizable block copolymer is adsorbed to the surface portion of the nanoparticle.

The drug, cellulosic polymer, and block copolymer are collectively present in the nanoparticle in an amount ranging from about 60 wt % to 100 wt %. Preferably, the drug, cellulosic polymer, and block copolymer collectively constitute at least 70 wt %, more preferably at least 80 wt %, and even more preferably at least 90 wt % of the nanoparticle. In one embodiment, the nanoparticles consist essentially of the drug, the non-ionizable cellulosic polymer and the amphiphilic non-ionizable block copolymer. By "consist essentially of" is meant that the nanoparticle contains less than 1 wt % of any other excipients and that any such excipients have no affect on the performance or properties of the nanoparticle.

The amount of drug in the nanoparticle may range from 0.1 wt % to 90 wt %. Preferably the amount of drug in the nanoparticle ranges from about 1 wt % to about 80 wt %, more preferably from about 5 wt % to about 75 wt %, and most preferably from about 10 wt % to about 67 wt %.

To minimize the total mass of the formulation, high drug loadings are desired. However, if the amount of drug in the nanoparticle is too high, the nanoparticle suspension becomes unstable, resulting in crystallization of the drug in the suspension. Additionally, high amounts of drug in the nanoparticle can lead to crystalline drug formation when the nanoparticles are isolated from suspension in solid form. In absolute terms, it is preferred that the amount of drug in the nanoparticle be less than about 90 wt %, more preferably less than about 80 wt %, even more preferably less than about 75 wt % the total mass of the nanoparticle.

The amount of poorly aqueous soluble non-ionizable cellulosic polymer may range from 10 wt % to 75 wt %. The physical stability of the non-crystalline drug in the nanoparticle tends to improve with increasing amounts of the poorly aqueous soluble non-ionizable cellulosic polymer. Accordingly, it is preferred that the amount of poorly aqueous soluble non-ionizable cellulosic polymer in the nanoparticle is at least 15 wt %, more preferably at least 20 wt %, and most preferably at least 25 wt %. However, too much non-ionizable cellulosic polymer will lead to low drug loading in the nanoparticle and low amounts of the amphiphilic non-ionizable block copolymer. Thus, it is preferred that the amount of poorly aqueous soluble non-ionizable cellulosic polymer in the nanoparticle is 75% or less, and most preferably 70 wt % or less.

The amount of poorly aqueous soluble polymeric amphiphilic non-ionizable block copolymer may range from 5 wt % to 80 wt %. Preferably, the amphiphilic non-ionizable block copolymer is present in a sufficient amount so that the nanoparticles do not agglomerate into larger particles in solution. Preferably the amount of amphiphilic non-ionizable block copolymer in the nanoparticle is at least 10 wt %, more preferably at least 15 wt %, and most preferably at least 20 wt %. However, too much amphiphilic non-ionizable block copolymer will lead to low drug loading and low amounts of the non-ionizable cellulosic polymer. Thus, it is preferred that the amount of amphiphilic non-ionizable block copolymer be 75 wt % or less, and most preferably 70 wt % or less.

Preferred embodiments of nanoparticles have the following amount of drug, poorly aqueous soluble non-ionizable cellulosic polymer and amphiphilic non-ionizable block copolymer:

1 to 80 wt %, preferably 5 to 75 wt %, more preferably 5 to 50 wt % drug;

10 to 75 wt %, preferably 20 to 60 wt %, more preferably 30 to 70 wt % poorly aqueous soluble non-ionizable cellulosic polymer, and 5 to 60 wt %, preferably 5 to 50 wt %, more preferably 5 to 30 wt % poorly aqueous soluble polymeric amphiphilic non-ionizable block copolymer.

The nanoparticle is preferably substantially free from ionizable surfactants. By a "surfactant" is meant a surface-active material with a molecular weight of less than about 2000 daltons having a hydrophobic portion and a hydrophilic portion, and which is soluble in the use environment. By "ionizable" is meant the surfactant has at least one ionizable group capable of being ionized over at least a portion of the pH range of 1 to 8 covalently attached to the surfactant. By substantially "free from" is meant that the amount of ionizable surfactant present in the composition is less than about 0.1 wt %. Preferably, the amount of ionizable surfactant present in the nanoparticles is less than the detection limit.

Non-Ionizable Cellulosic Polymers

The nanoparticles of the present invention comprise a poorly aqueous soluble non-ionizable cellulosic polymer having an ether- or ester-linked alkyl substituent. The term "polymer" is used conventionally, meaning a compound that is made of monomers connected together to form a larger molecule. A polymer generally consists of at least about 20 monomers connected together. Thus, the molecular weight of the polymer generally will be about 2000 daltons or more. The polymer should be inert, in the sense that it does not chemically react with the drug in an adverse manner, and should be pharmaceutically acceptable.

The polymer is a poorly aqueous soluble non-ionizable cellulosic polymer. By "poorly aqueous soluble" is meant that the polymer has a solubility of less than 0.1 mg/mL when administered alone at a concentration of 0.2 mg/mL to a phosphate buffered saline solution (PBS) at pH 6.5. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. A test to determine whether the cellulosic polymer is insoluble may be performed as follows. The cellulosic polymer is initially present in bulk powder form with average particle sizes of greater than about 1 micron. The polymer alone is administered at a concentration of 0.2 mg/mL to the PBS solution and stirred for approximately 1 hour at room temperature. Next, a nylon 0.45 μm filter is weighed, and the solution is filtered. The filter is dried overnight at 40° C., and weighed the following morning. The amount of polymer dissolved is calculated from the amount of polymer added to the PBS solution minus the amount of polymer remaining on the filter (mg). The cellulosic polymer is considered to be poorly aqueous soluble if it has a solubility of less than 0.1 mg/mL in this test. Preferably, when administered at a concentration of 0.2 mg/mL to the pH 6.5 PBS, a poorly aqueous soluble non-ionizable cellulosic polymer has a solubility of less than 0.07 mg/mL, more preferably less than 0.05 mg/mL, and most preferably less than 0.01 mg/mL.

To ease processing, it is preferred that the poorly aqueous soluble non-ionizable cellulosic polymer be soluble in an organic solvent. Preferably the cellulosic polymer has a solubility in an organic solvent of at least about 0.1 mg/mL, and preferably at least 1 mg/mL. Preferably the polymer is not crosslinked.

The polymer is "non-ionizable," meaning that the polymer possesses substantially no ionizable functional groups. By "substantially no ionizable functional groups" is meant that the number of ionizable groups covalently attached to the cellulosic polymer is less than about 0.05 milliequivalents per gram of polymer. Preferably, the number is less than about 0.02 milliequivalents per gram of polymer. By " ionizable groups" is meant functional groups that are at least about 10% ionized over at least a portion of the physiologically relevant pH range of 1 to 8. Such groups have $pK_a$ values of about 0 to 9.

The polymer is a poorly aqueous soluble non-ionizable cellulosic polymer having an ether- or ester-linked alkyl substituent. Suitable alkyl substituents include $C_1$ to $C_4$ alkyl groups. Exemplary ether-linked alkyl substituents include methyl, ethyl, propyl, and butyl groups. Exemplary ester-linked alkyl substituents include acetate, propionate, and butyrate groups.

Exemplary non-ionizable cellulosic polymers include methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, and hydroxypropyl methylcellulose butyrate. Preferably the poorly aqueous soluble non-ionizable cellulosic polymer is selected from the group consisting of ethyl cellulose, cellulose acetate, cellulose propionate, cellulose butyrate, and cellulose acetate butyrate. Preferably, the poorly aqueous soluble non-ionizable cellulosic polymer is ethyl cellulose.

Amphiphilic Non-Ionizable Block Copolymers

The nanoparticles also comprise a poorly aqueous soluble polymeric amphiphilic non-ionizable block copolymer. The block copolymer has a hydrophobic block that is a polylactone, and a hydrophilic block that is polyethylene oxide (PEO), which may also be termed polyethylene glycol (PEG) depending on the monomer used to form the block. The amphiphilic non-ionizable block copolymer is present in a sufficient amount to reduce or prevent aggregation or agglomeration of the nanoparticles while in suspension. This results in nanoparticles with improved stability. The block copolymer should be inert, in the sense that it does not chemically react with the drug in an adverse manner, and should be pharmaceutically acceptable.

The block copolymer is "amphiphilic" in nature, meaning that the block copolymer has hydrophilic and hydrophobic portions. Without wishing to be bound by any theory or mechanism of action, it is believed that the hydrophobic portion of the amphiphilic block copolymer is associated with the core of the nanoparticle, while the hydrophilic portion of the amphiphilic block copolymer is associated with the surface portion of the nanoparticle and can interact with water when the nanoparticles are in an aqueous suspension. The amphiphilic nature of the material helps stabilize the nanoparticles in suspension, reducing or preventing agglomeration of the nanoparticles.

The block copolymer is also "non-ionizable," meaning that the block copolymer possesses substantially no ionizable functional groups. By "substantially no ionizable functional groups" is meant that the number of ionizable groups covalently attached to the block copolymer is less than about 0.05 milliequivalents per gram of block copolymer. Preferably, the number is less than about 0.02 milliequivalents per gram of block copolymer. By "ionizable groups" is meant functional groups that are at least about 10% ionized over at least a portion of the physiologically relevant pH range of 1 to 8. Such groups have $pK_a$ values of about 0 to 9.

The amphiphilic non-ionizable block copolymer is also poorly aqueous soluble, as described above for the poorly aqueous soluble non-ionizable cellulosic polymer. Thus, when the block copolymer is administered alone at a concentration of 0.2 mg/mL to a PBS solution at pH 6.5, the block copolymer has a solubility of less than 0.1 mg/mL. In one preferred embodiment, when administered at a concentration of 0.2 mg/mL to the PBS solution, the block copolymer has a solubility of less than 0.07 mg/mL, more preferably less than 0.05 mg/mL, and most preferably less than 0.01 mg/mL.

The molecular weight of the block copolymer may vary, but generally is greater than about 2,000 daltons. In one embodiment, the amphiphilic non-ionizable block copolymer has a high molecular weight, meaning that the molecular weight of the block copolymer is at least 5,000 daltons, preferably at least 7,000 daltons, and more preferably is at least 10,000 daltons. Block copolymers may be diblock copolymers, tri-block copolymers, and other block copolymers known in the art.

The amphiphilic non-ionizable block copolymer has at least one hydrophilic block and at least one hydrophobic block. The hydrophobic block is a polylactone, such as poly (lactide), poly(glycolide), poly($\epsilon$-caprolactone), and copolymers of these, including poly(lactide-co-glycolide), poly(lactide-co-$\epsilon$-caprolactone), and mixtures thereof. The hydrophilic block is PEO, which is also known as PEG.

Exemplary poorly aqueous soluble polymeric amphiphilic non-ionizable block copolymers include poly(ethylene oxide-b-$\epsilon$-caprolactone) (also known as poly($\epsilon$-caprolactone-b-ethylene glycol) or pCL-PEG), poly(ethylene oxide-b-lactide), poly(lactide-b-ethylene glycol), poly(ethylene oxide-b-glycolide), poly(glycolide-b-ethylene glycol), poly (ethylene oxide-b-lactide-co-glycolide), poly(lactide-co-glycolide-b-ethylene glycol), and mixtures thereof.

In a preferred embodiment, the amphiphilic non-ionizable block copolymer is poly(ethylene oxide-b-$\epsilon$-caprolactone).

In one embodiment, the non-ionizable cellulosic polymer is selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, hydroxypropyl methylcellulose acetate, hydroxypropyl methylcellulose propionate, hydroxypropyl methylcellulose butyrate, and the poorly aqueous soluble polymeric amphiphilic non-ionizable block copolymer is selected from the group consisting of poly(ethylene oxide-b-$\epsilon$-caprolactone), poly($\epsilon$-caprolactone-b-ethylene glycol), poly(ethylene oxide-b-lactide), poly(lactide-b-ethylene glycol), poly(ethylene oxide-b-glycolide), poly(glycolide-b-ethylene glycol), poly(ethylene oxide-b-lactide-co-glycolide), poly(lactide-co-glycolide-b-ethylene glycol), and mixtures thereof.

In another embodiment, the non-ionizable cellulosic polymer is selected from the group consisting of ethylcellulose, cellulose acetate, cellulose propionate, cellulose butyrate, cellulose acetate butyrate, and mixtures thereof, and the poorly aqueous soluble polymeric amphiphilic non-ionizable block copolymer is selected from the group consisting of poly(ethylene oxide-b-$\epsilon$-caprolactone), poly($\epsilon$-caprolactone-b-ethylene glycol), poly(ethylene oxide-b-lactide), poly(lactide-b-ethylene glycol), poly(ethylene oxide-b-glycolide), poly(glycolide-b-ethylene glycol), poly(ethylene oxide-b-lactide-co-glycolide), poly(lactide-co-glycolide-b-ethylene glycol), and mixtures thereof.

In still another embodiment, the non-ionizable cellulosic polymer is selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, and the poorly aqueous soluble polymeric amphiphilic non-ionizable block copolymer is poly(ethylene oxide-b-$\epsilon$-caprolactone).

In yet another embodiment, the non-ionizable cellulosic polymer is selected from the group consisting of ethylcellulose, cellulose acetate, cellulose propionate, cellulose butyrate, cellulose acetate butyrate, and mixtures thereof, and the poorly aqueous soluble polymeric amphiphilic non-ionizable block copolymer is poly(ethylene oxide-b-$\epsilon$-caprolactone).

In still another embodiment, the non-ionizable cellulosic polymer is ethylcellulose and the poorly aqueous soluble polymeric amphiphilic non-ionizable block copolymer is poly(ethylene oxide-b-$\epsilon$-caprolactone).

The Drug

The drug is a "poorly water soluble drug," meaning that the drug has a solubility in water of less than 5 mg/mL over the pH range of 6.5 to 7.5 at 25° C. The utility of the invention increases as the water solubility of the drug decreases. The drug may have an even lower solubility in water, such as less than about 1 mg/mL, less than about 0.1 mg/mL, and even less than about 0.01 mg/mL.

In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, anti-obesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, and antiviral agents.

Each named drug should be understood to include the nonionized form of the drug or pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Exemplary drugs suitable for use in the nanoparticles include, but are not limited to, phosphodiesterase inhibitors, such as sildenafil and sildenafil citrate; HMG-CoA reductase inhibitors, such as atorvastatin, lovastatin, simvastatin, pravastatin, fluvastatin, rosuvastatin, itavastatin, nisvastatin, visastatin, atavastatin, bervastatin, compactin, dihydrocompactin, dalvastatin, fluindostatin, pitivastatin, and velostatin (also referred to as synvinolin); vasodilator agents, such amiodarone; antipsychotics, such as ziprasidone; calcium channel blockers, such as nifedipine, nicardipine, verapamil, and amlodipine; cholesteryl ester transfer protein (CETP) inhibitors; cyclooxygenase-2 inhibitors; microsomal triglyceride transfer protein (MTP) inhibitors; vascular endothelial growth factor (VEGF) receptor inhibitors; carbonic anhydrase inhibitors; and glycogen phosphorylase inhibitors. Other low-solubility drugs suitable for use in the nanoparticles are disclosed in US Published patent application 2005/0031692, herein incorporated by reference.

In one embodiment, the drug is ziprasidone or a pharmaceutically acceptable form thereof.

In another embodiment, the drug is a hydrophobic non-ionizable drug. By "hydrophobic non-ionizable drug" is meant a subclass of non-ionizable drugs that are essentially water insoluble and highly hydrophobic, and are characterized by a set of physical properties, as described hereinafter. By "non-ionizable" is meant that the drug has substantially no ionizable groups. By "ionizable groups" is meant functional groups that are at least about 10% ionized over at least a portion of the physiologically relevant pH range of 1 to 8. Such groups have pKa values of about 0 to 9. Thus, hydrophobic non-ionizable drugs do not have a pKa value between 0 and 9.

The first property of hydrophobic drugs is that they are extremely hydrophobic. Log P, defined as the base 10 logarithm of the ratio of the drug solubility in octanol to the drug solubility in water, is a widely accepted measure of hydrophobicity. By "extremely hydrophobic" is meant that the Log P value of the drug is at least 4.0, preferably at least 4.5, and most preferably at least 5.0. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 J. Chem. Inf. Comput. Sci. 21 (1987)); Viswanadhan's fragmentation method (29 J. Chem. Inf. Comput. Sci. 163 (1989)); or Broto's fragmentation method (19 Eur. J. Med. Chem.-Chim. Theor. 71 (1984).

The second property of hydrophobic drugs is that they have an extremely low solubility in water over the pH range of 6.5 to 7.5 at 25° C. By "extremely low solubility in water" is meant that the solubility of the drug in water is less than 100 μg/mL. Preferably, the hydrophobic drug has a water solubility of less than 50 μg/mL, and most preferably less than 10 μg/mL.

In another embodiment the drug is a cholesteryl ester transfer protein (CETP) inhibitor. CETP inhibitors are drugs that inhibit CETP activity. The effect of a drug on the activity of CETP can be determined by measuring the relative transfer ratio of radiolabeled lipids between lipoprotein fractions, essentially as previously described by Morton in *J. Biol. Chem.* 256, 11992, 1981 and by Dias in *Clin. Chem.* 34, 2322, 1988, and as presented in U.S. Pat. No. 6,197,786, the disclosures of which are herein incorporated by reference. The potency of CETP inhibitors may be determined by performing the above-described assay in the presence of varying concentrations of the test compounds and determining the concentration required for 50% inhibition of transfer of radiolabeled lipids between lipoprotein fractions. This value is defined as the "$IC_{50}$ value." Preferably, the CETP inhibitor has an $IC_{50}$ value of less than about 2000 nM, more preferably less than about 1500 nM, even more preferably less than about 1000 nM, and most preferably less than about 500 nM.

Specific examples of CETP inhibitors include [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester; (2R)-3-[[3-(4-chloro-3-ethylphenoxy)phenyl][[3-(1,1,2,2-tetrafluoroethoxy)phenyl]methyl]amino]-1,1,1-trifluoro-2-propanol; S-[2-([[1-(2-ethylbutyl)cyclohexyl]carbonyl]amino)phenyl]2-methylpropanethioate; trans-4-[[[2-[[[[3,5-bis(trifluoromethyl)phenyl]methyl](2-methyl-2H-tetrazol-5-yl)amino]methyl]-4-(trifluoromethyl)phenyl]ethylamino]methyl]-cyclohexaneacetic acid; trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl)acetic acid methanesulfonate; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide; methyl N-(3-cyano-5-trifluoromethylbenzyl)-[6-(N'-cyclopentylmethyl-N'-ethylamino)indan-5-ylmethyl]-carbamate; methyl (3-cyano-5-trifluoromethylbenzyl)-[6-(N-cyclopentylmethyl-N-ethylamino)indan-5-ylmethyl]-carbamate; ethyl 4-((3,5-bis(trifluoromethyl)phenyl)(2-methyl-2H-tetrazol-5-yl)methyl)-2-ethyl-6-(trifluoromethyl)-3,4-dihydroquinoxaline-1(2H)-carboxylate; tert-butyl 5-(N-(3,5-bis(trifluoromethyl)benzyl)acetamido)-7-methyl-8-(trifluoromethyl)-2,3,4,5-tetrahydrobenzo[b]azepine-1-carboxylate; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; the drugs disclosed in commonly owned U.S. patent application Ser. Nos. 09/918,127 and 10/066,091, the disclosures of both of which are incorporated herein by reference; and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; JP 11049743; WO 0018721; WO 0018723; WO 0018724; WO 0017164; WO 0017165; WO 0017166; EP 992496; EP 987251; WO 9835937; JP 03221376; WO 04020393; WO 05095395; WO 05095409; WO 05100298; WO 05037796; WO 0509805; WO 03028727; WO 04039364; WO 04039453; WO 0633002; and U.S. Provisional Patent Application Nos. 60/781,488 and 60/780,993, both of which were filed on Mar. 10, 2006.

Thus, in one embodiment, the CETP inhibitor is selected from the group of compounds mentioned above. In another embodiment, the CETP inhibitor is selected from the group consisting of (2R)-3-[[3-(4-chloro-3-ethylphenoxy)phenyl][[3-(1,1,2,2-tetrafluoroethoxy)phenyl]methyl]amino]-1,1,1-trifluoro-2-propanol; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2- methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; and pharmaceutically acceptable forms thereof.

In still another embodiment, the CETP inhibitor is (2R)-3-[[3-(4-chloro-3-ethylphenoxy)phenyl][[3-(1,1,2,2-tetrafluoroethoxy)phenyl]methyl]amino]-1,1,1-trifluoro-2-propanol.

In still another embodiment, the CETP inhibitor is trans-(2R,4S)-2-(4-{4-[(3,5-Bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide.

In another embodiment, the drug is an inhibitor of cyclooxygenase-2 (COX-2). COX-2 inhibitors are nonsteroidal anti-inflammatory drugs that exhibit anti-inflammatory, analgesic and antipyretic effects. Preferably, the COX-2 inhibitor is a selective COX-2 inhibitor, meaning that the drug is able to inhibit COX-2 without significant inhibition of cyclooxygenase-1 (COX-1). Preferably, the COX-2 inhibitor has a potency such that the concentration of drug that inhibits 50% of COX-2 enzyme in an in vitro test (i.e., the $IC_{50}$ value) is less than about 10 µM, preferably less than 5 µM, more preferably less than 2 µM. In addition, it is also preferable that the COX-2 inhibitor be selective relative to COX-1. Thus, preferably, the ratio of the $IC_{50,COX-2}$ to $IC_{50,COX-1}$ ratio for the compound is less than 0.5, more preferably than 0.3, and most preferably less than 0.2.

Specific examples of COX-2 inhibitors include 4-(5-(4-methylphenyl)-3-(trifluoromethyl)-1H-pyrazol-1-yl)benzenesulfonamide (celecoxib); 4-(5-methyl-3-phenylisoxazol-4-yl)benzenesutfonamide (valdecoxib); N-(4-(5-methyl-3-phenylisoxazol-4-yl)phenylsulfonyl)propionamide (paracoxb); sodium (S)-6,8-dichloro-2-(trifluoromethyl)-2H-chromene-3-carboxylate; sodium (S)-7-tert-butyl-6-chloro-2-(trifluoromethyl)-2H-chromene-3-carboxylate; 2-[(2-chloro-6-fluorophenyl)amino]-5-methyl benzeneacetic acid (lumiracoxib); 4-(3-(difluoromethyl)-5-(3-fluoro-4-methoxyphenyl)-1H-pyrazol-1-yl)benzenesulfonamide (deracoxib); 4-(4-(methylsulfonyl)phenyl)-3-phenylfuran-2(5H)-one (rofecoxib); 5-chloro-2-(6-methylpyridin-3-yl)-3-(4-(methylsulfonyl)phenyl)pyridine (etoricoxib); 2-(3,4-difluorophenyl)-4-(3-hydroxy-3-methylbutoxy)-5-(4-(methylsulfonyl)phenyl)pyridazin-3(2H)-one; (Z)-3-((3-chlorophenyl)(4-(methylsulfonyl)phenyl)methylene)-dihydrofuran-2(3H)-one; N-(2-(cyclohexyloxy)-4-nitrophenyl)methanesutfonamide; 4-Methyl-2-(3,4-dimethylphenyl)-1-(4-sulfamoyl-phenyl)-1H-pyrrole; 6-((5-(4-chlorobenzoyl)-1,4-dimethyl-1H-pyrrol-2-yl)methyl)pyridazin-3(2H)-one; 4-(4-cyclohexyl-2-methyloxazol-5-yl)-2-fluorobenzenesuffonamide (tilmacoxib); 2-(4-Ethoxyphenyl)-4-methyl-1-(4-sulfamoylphenyl)-1H-pyrrole; 4-hydroxy-2-methyl-N-(5-methyl-2-thiazolyl)-2H-1,2-benzothiazine-3-carboxamide-1,1-dioxide (meloxicam); 4-(4-chloro-5-(3-fluoro-4-methoxyphenyl)-1H-pyrazol-1-yl)benzenesulfonamide (cimicoxib), and pharmaceutically acceptable forms thereof; and the compounds disclosed in the following patents and published applications, the disclosures of which are incorporated herein by reference: U.S. Pat. Nos. 5,466,823, 5,633,272, 5,932,598, 6,034,256, 6,180,651, 5,908,858, 5,521,207, 5,691,374, WO 99/11605, WO 98/03484, and WO 00/24719.

Preferably the COX-2 inhibitor is selected from the group consisting of celecoxib; valdecoxib; paracoxb; sodium (S)-6,8-dichloro-2-(trifluoromethyl)-2H-chromene-3-carboxylate; sodium (S)-7-tert-butyl-6-chloro-2-(trifluoromethyl)-2H-chromene-3-carboxylate; and pharmaceutically acceptable forms thereof. In one embodiment, the COX-2 inhibitor is celecoxib or pharmaceutically acceptable forms thereof.

Process for Forming Nanoparticles

The nanoparticles may be formed by any process that results in formation of nanoparticles of non-crystalline drug, a non-ionizable cellulosic polymer, and an amphiphilic non-ionizable block copolymer. The drug used to form the nanoparticles may be in a crystalline or non-crystalline form; however, at least 90 wt % of the drug in the resulting nanoparticles is in non-crystalline form.

One process for forming nanoparticles is an emulsification process. In this process, the drug, the non-ionizable cellulosic polymer, and the amphiphilic non-ionizable block copolymer are dissolved in an organic solvent that is immiscible with an aqueous solution in which the drug, cellulosic polymer, and amphiphilic non-ionizable block copolymer are poorly soluble, forming an organic solution. Solvents suitable for forming the solution of dissolved drug and cellulosic polymer can be any compound or mixture of compounds in which the drug and the cellulosic polymer are mutually soluble and which is immiscible with the aqueous solution. As used herein, the term "immiscible" means that the solvent has a solubility in the aqueous solution of less than about 10 wt %, preferably less than about 5 wt %, and most preferably less than about 3 wt %. Preferably, the solvent is also volatile with a boiling point of 150° C. or less. Exemplary solvents include methylene chloride, trichloroethylene, trichloro-trifluoroethylene, tetrachloroethane, trichloroethane, dichloroethane, dibromoethane, ethyl acetate, phenol, chloroform, toluene, xylene, ethyl-benzene, benzyl alcohol, creosol, methyl-ethyl ketone, methyl-isobutyl ketone, hexane, heptane, ether, and mixtures thereof. Preferred solvents are methylene chloride, ethyl acetate, benzyl alcohol, and mixtures thereof. The aqueous solution is preferably water.

The organic solution is mixed with the aqueous solution and homogenized to form an emulsion of fine droplets of the organic solution distributed throughout the aqueous phase. The volume ratio of organic solution to aqueous solution used in the process will generally range from 1:100 (organic solution:aqueous solution) to 2:3 (organic solution:aqueous solution). Preferably, the organic solution:aqueous solution volume ratio ranges from 1:9 to 1:2 (organic solution:aqueous solution). The emulsion is generally formed by a two-step homogenization procedure. The organic solution and aqueous solution are first mixed using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration. Preferably, the organic solvent is removed to a level that is acceptable according to The International Committee on Harmonization (ICH) guidelines. Preferably, the concentration of solvent in the nanoparticle suspension is less than the solubility of the solvent in the aqueous solution. Even lower concentrations of solvent are preferred. Thus, the concentration of organic solvent in the nanoparticle suspension may be less than about 5 wt %, less than about 3 wt %, less than 1 wt %, and even less than 0.1 wt %.

Alternatively, the drug and non-ionizable cellulosic polymer are dissolved in an organic solvent that is immiscible with the aqueous solution, while the amphiphilic non-ionizable block copolymer is suspended in the aqueous solution. The nanoparticles are then formed using the above emulsification procedure.

An alternative process to form the nanoparticles is a precipitation process. In this process, the drug, non-ionizable cellulosic polymer, and amphiphilic non-ionizable block copolymer are first dissolved in a solvent that is miscible with an aqueous solution in which the drug, cellulosic polymer, and block copolymer are poorly soluble. The resulting organic solution is mixed with the aqueous solution causing the nanoparticles to precipitate. Solvents suitable for forming the solution of dissolved drug, non-ionizable cellulosic polymer, and amphiphilic non-ionizable block copolymer can be any compound or mixture of compounds in which the drug, polymer, and block copolymer are mutually soluble and which is miscible in the aqueous solution. Preferably, the organic solvent is also volatile with a boiling point of 150° C. or less. Exemplary solvents include acetone, methanol, ethanol, tetrahydrofuran (THF), and dimethylsulfoxide (DMSO). Mixtures of solvents, such as 50% methanol and 50% acetone, can also be used, so long as the drug, polymer, and block copolymer are sufficiently soluble to dissolve the drug and polymer. Preferred solvents are methanol, acetone, and mixtures thereof.

The aqueous solution may be any compound or mixture of compounds in which the drug, polymer, and block copolymer are sufficiently insoluble so as to precipitate to form nanoparticles. The aqueous solution preferably is water.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

For the precipitation process, the amount of drug, cellulosic polymer, and block copolymer in the solvent solution depends on the solubility of each in the organic solvent and the desired ratios of drug to cellulosic polymer to block copolymer in the resulting nanoparticles. The solution may comprise from about 0.1 wt % to about 20 wt % dissolved solids. A dissolved solids content of from about 0.5 wt % to 10 wt % is preferred.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2 (organic solution:aqueous solution). Preferably, the organic solution:aqueous solution volume ratio ranges from about 1:20 to about 1:3.

Alternatively, the drug and non-ionizable cellulosic polymer are dissolved in the organic solvent, while the amphiphilic non-ionizable block copolymer is suspended in the aqueous solution. The nanoparticles are then formed using the above precipitation procedure.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. Preferably, the solvent is removed to a level that is acceptable according to ICH guidelines. Thus, the concentration of organic solvent in the nanoparticle suspension may be less than about 10 wt %, less than about 5 wt %, less than about 3 wt %, less than 1 wt %, and even less than 0.1 wt %.

In one embodiment, a process for forming nanoparticles, comprises: (a) forming an organic solution comprising a poorly water soluble drug and a poorly aqueous soluble non-ionizable cellulosic polymer dissolved in a solvent, wherein the drug has a solubility in water of less than 5 mg/mL over the pH range of 6.5 to 7.5 at 25° C.; (b) forming an aqueous solution, wherein the drug and the non-ionizable cellulosic polymer are poorly soluble in the aqueous solution; (c) adding an amphiphilic non-ionizable block copolymer to at least one of the organic solution and the aqueous solution; (d) mixing the organic solution with the aqueous solution to form a first mixture; (e) removing the solvent from the first mixture to form a suspension comprising the nanoparticles and the aqueous solution, wherein (i) the nanoparticles have an average size of less than 500 nm, (ii) at least 90 wt % of the drug in the nanoparticles is non-crystalline, and (iii) the drug, the non-ionizable cellulosic polymer, and the amphiphilic non-ionizable block copolymer collectively constitute at least 60 wt % of the nanoparticles.

Both the emulsion process and the precipitation process result in the formation of a suspension of the nanoparticles in the aqueous solution. In some instances it is desirable to concentrate the nanoparticles or to isolate the nanoparticles in solid form by removing some or all of the liquid from the suspension. Exemplary processes for removing at least a portion of the liquid include spray drying, spray coating, spray layering, lyophylization, evaporation, vacuum evaporation, filtration, ultrafiltration, reverse osmosis, and other processes known in the art. Preferably, the liquid is removed by a process selected from spray drying, evaporation, and lyophylization. In one embodiment, the liquid is removed by spray drying. In another embodiment, the liquid is removed by evaporation. In still another embodiment, the liquid is removed by lyophylization. In yet another embodiment, the liquid is removed by a combination of processes selected from the group consisting of spray drying, spray coating, spray layering, lyophylization, evaporation, vacuum evaporation, filtration, ultrafiltration, reverse osmosis, and other processes known in the art. For example, the liquid may be removed by ultrafiltration, followed by spray drying, followed by evaporation in a tray dryer.

When isolating the nanoparticles in solid form, it is often desirable to include a matrix material in the suspension of nanoparticles prior to removal of the liquids. The matrix material functions to help slow or prevent agglomeration of the nanoparticles as the liquids are being removed, as well as to help re-suspend the nanoparticles when the solid composition is added to an aqueous solution (e.g., an aqueous environment of use). The matrix material is preferably pharmaceutically acceptable and water soluble. Examples of matrix materials include polyvinyl pyrrolidone (PVP), trehalose, hydroxypropyl methyl cellulose (HPMC), hydroxypropyl cellulose (HPC), casein, caseinate, albumin, gelatin, acacia, lactose, mannitol, and other matrix materials know in the art, and pharmaceutically acceptable forms and mixtures thereof. Preferably, the matrix material is selected from the group consisting of casein, caseinate, and pharmaceutically acceptable forms or mixtures thereof.

In one embodiment of the invention, a solid composition comprises (a) a plurality of nanoparticles comprising a poorly water-soluble drug, a non-ionizable cellulosic polymer, and an amphiphilic non-ionizable block copolymer, and (b) a matrix material. As used herein, the term "solid pharmaceutical composition" means that the composition is in a solid form and substantially free of liquids. The nanoparticles are entrapped or encapsulated in the matrix material.

The presence of nanoparticles in the solid composition can be determined using the following procedure. A sample of the solid composition is embedded in a suitable material, such as an epoxy or polyacrylic acid (e.g., L R White from London Resin Co., London, England). The sample is then microtomed to obtain a cross-section of the solid composition that is about 100 to 200 nm thick. This sample is then analyzed using transmission electron microscopy (TEM) with energy dispersive X-ray (EDX) analysis. TEM-EDX analysis quantitatively measures the concentration and type of atoms larger than boron over the surface of the sample. From this analysis, regions that are rich in drug can be distinguished from regions that are rich in the matrix material. The size of the regions that are rich in drug will have an average diameter of less than 500 nm in this analysis, demonstrating that the solid composition comprises nanoparticles of drug in the matrix material. See, for example, *Transmission Electron Microscopy and Diffractometry of Materials* (2001) for further details of the TEM-EDX method.

Another procedure that demonstrates the solid composition contains nanoparticles is to administer a sample of the solid composition to water to form a suspension of the nanoparticles. The suspension is then analyzed by DLS as described herein. A solid composition of the invention will form nanoparticles having an average cumulant diameter of less than 500 nm.

A specific procedure for demonstrating the solid composition contains nanoparticles is as follows. A sample of the solid composition is added to water at ambient temperature such that the concentration of solids is less than about 1 mg/mL. The so-formed suspension is then analyzed by DLS. The solid composition contains nanoparticles if the DLS analysis results in particles having an average cumulant diameter of less than 500 nm.

A solid composition of the invention will show the presence of nanoparticles in at least one, and preferably both of the above tests.

Dosage Forms

The nanoparticles may be administered using any known dosage form. The nanoparticles may be formulated for administration via oral, topical, subdermal, intranasal, buccal, intrathecal, ocular, intraaural, intraarticular, subcutaneous spaces, vaginal tract, arterial and venous blood vessels, pulmonary tract or intramuscular tissue of an animal, such as a mammal and particularly a human. Oral dosage forms include: powders or granules; tablets; chewable tablets; capsules; unit dose packets, sometimes referred to in the art as "sachets" or "oral powders for constitution" (OPC); syrups; and suspensions. Parenteral dosage forms include reconstitutable powders or suspensions. Topical dosage forms include creams, pastes, suspensions, powders, foams and gels. Ocular dosage forms include suspensions, emulsions, powders, gels, creams, pastes, solid inserts, depots, and implants.

In one embodiment, the compositions of the present invention are capable of improving the concentration of dissolved drug in a use environment relative to a control composition consisting essentially of the drug alone without any of the polymers. In order to determine concentration enhancement in vitro, the amount of "free" drug, or solvated drug is measured. By "free" drug is meant drug which is in the form of dissolved drug or present in micelles, but which is not in the nanoparticles or any solid particles larger than 500 nm, such as precipitate. A composition of the invention provides concentration enhancement if, when administered to an aqueous use environment, it provides a free drug concentration that is at least 1.25-fold the free drug concentration provided by the control composition. Preferably, the free drug concentration provided by the compositions of the invention are at least about 1.5-fold, more preferably at least about 2-fold, and most preferably at least about 3-fold that provided by the control composition.

Alternatively, the compositions of the present invention, when dosed orally to a human or other animal, provide an AUC in drug concentration in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. The determination of AUCs is a well-known procedure and is described, for example, in Welling, "Pharmacokinetics Processes and Mathematics," ACS Monograph 185 (1986).

Alternatively, the compositions of the present invention, when dosed orally to a human or other animal, provide a maximum drug concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

Without further elaboration, it is believed that one of ordinary skill in the art can, using the foregoing description, utilize the present invention to its fullest extent Therefore, the following specific embodiments are to be construed as merely illustrative and not restrictive of the scope of the invention. Those of ordinary skill in the art will understand that variations of the conditions and processes of the following examples can be used.

EXAMPLES

Drugs Used in Examples

The following drugs were used in the examples described below.

Drug 1 was 4-(5-methyl-3-phenyl-4-isoxazolyl)benzenesulfonamide, also known as valdecoxib, having the structure:

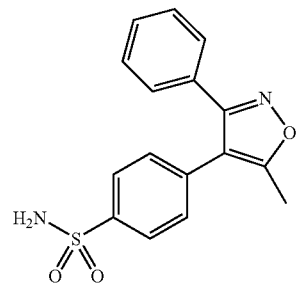 [SMILES: Cc1onc(-c2ccccc2)c1-c1ccc(S(N)(=O)=O)cc1]

Drug 1 has a solubility in water of about 10 μg/mL, and a Log P value of about 3.0. The $T_g$ of non-crystalline Drug 1 was determined by DSC analysis to be 55° C., while the $T_m$ of crystalline Drug 1 was 170° C.

Drug 2 was [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, having the structure:

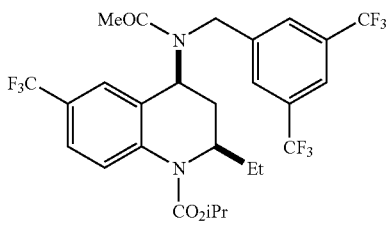

Drug 2 has a solubility in water of less than 1 μg/mL, and a Log P value of 6.7. The $T_g$ of non-crystalline Drug 2 was determined by DSC analysis to be 46° C., while the $T_m$ of crystalline Drug 2 was 111° C.

Drug 3 was celecoxib, having the structure:

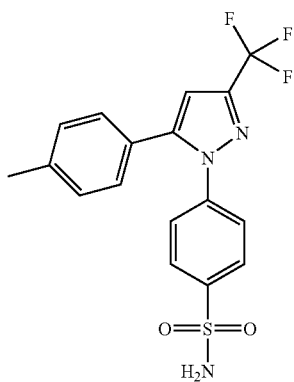 [SMILES: Cc1ccc(-c2cc(C(F)(F)F)nn2-c2ccc(S(N)(=O)=O)cc2)cc1]

Drug 3 has a solubility in a model fasted duodenal (MFD) solution (phosphate buffered saline [PBS] containing 7.3 mM sodium taurocholic acid and 1.4 mM of 1-palmitoyl-2-oleyl-sn-glycero-3-phosphocholine) of about 40 μg/mL, and a LogP value of 3.75. The $T_g$ of non-crystalline Drug 3 was determined by DSC analysis to be 54° C., while the $T_m$ of crystalline Drug 3 was 158° C.

Polymers Used in Examples

The following poorly aqueous soluble non-ionizable cellulosic polymers were used in the examples: ethylcellulose (ETHOCEL® Viscosity 4, Dow Chemical Co., Midland, Mich.); cellulose acetate (CA 398-10NF, available from Eastman Chemical Co., Kingsport, Tenn.); cellulose acetate butyrate (CAB-551-0.01, available from Eastman Chem. Co.).

These polymers were evaluated using the following procedure to verify that they are poorly aqueous soluble. First, 0.2 mg/mL of the polymer was added to a PBS solution consisting of 20 mM Na2HPO4, 47 mM KH2PO4, 87 mM NaCl, and 0.2 mM KCl, adjusted to pH 6.5 with NaOH. The polymer was stirred in the PBS solution for approximately 1 hour at room temperature. Next, the polymer solution was filtered through a nylon 0.45 μm filter that was weighed dry prior to filtration. The filter was dried overnight at 40° C., and weighed the following morning. The amount of soluble polymer was calculated from the amount of polymer added to form the polymer solution minus the amount of polymer remaining on the filter. The results of these tests are shown in Table 1 and show that all of the polymers tested are poorly aqueous soluble.

TABLE 1

| Example Polymer | Amount Soluble at pH 6.5 (mg/mL) | Observations |
| --- | --- | --- |
| Ethylcellulose | <0.001 | Fine particle suspension |
| Cellulose Acetate | 0.03 | Fine particle suspension |
| Cellulose Acetate Butyrate | 0.01 | Fine particle suspension |
| PLGA | 0.02 | Fine particle suspension |
| PVP | 0.2 | Polymer dissolved |

Two control polymers were also used in the examples. The first was poly(DL-lactide-co-glycolide 50:50) (PLGA, RESOMER® RG 502H, Boehringer Ingelheim Pharma, Germany). This polymer is not a cellulosic polymer. The aqueous solubility of the PLGA was determined using the above procedure and the results, presented in Table 1, show that PLGA is poorly aqueous soluble.

The second control polymer was polyvinyl pyrrolidone (PVP, K29/32, ISP Technologies, Wayne, N.J.). PVP is not a cellulosic polymer. In addition, PVP is not poorly aqueous soluble, as shown in Table 1.

Block Copolymers Used in Examples

The following amphiphilic non-ionizable block copolymers were used in the examples: poly(ethylene oxide-b-ε-caprolactone) (pCL-PEG, grade P3128-EOCL available from Polymer Source Inc., Montreal, Quebec, Canada), having an ε-caprolactone molecular weight of 10,000 daltons and an ethylene oxide molecular weight of 5,000 daltons; and poly (DL-lactide-co-glycolide-b-ethylene glycol) (PLGA-PEG; RESOMER® PEG RGP 50155, Boehringer Ingelheim Pharma, Germany), a block copolymer having a PLGA block (50:50 lactide:glycolide), and 15% of a PEG 5000 block.

The aqueous solubility of these amphiphilic non-ionizable block copolymers was determined using the above procedure; the results are summarized in Table 2. These results show that the pCL-PEG and PLGA-PEG block copolymers are poorly aqueous soluble.

TABLE 2

| Example Material | Soluble at pH 6.5 (mg/mL) | Observations |
| --- | --- | --- |
| pCL-PEG | 0.02 | Fine particle suspension |
| PLGA-PEG | 0.03 | Fine particle suspension |
| PEG 8000 | 0.2 | Stabilizer dissolved |

Polyethylene glycol 8000 (PEG 8000, available from Spectrum Chemical, Gardena, Calif.) was used as a control in the examples. PEG 8000 is aqueous soluble, as shown in Table 2.

Example 1

Nanoparticles containing valdecoxib ("Drug 1") were prepared as follows. First, 20.1 mg valdecoxib, 40.3 mg ethylcellulose, and 20.0 mg pCL-PEG were dissolved in 4 mL ethyl acetate to form an organic solution. The organic solution was then poured into 20 mL deionized water and emulsified for 4 min using a Kinematica Polytron 3100 rotor/stator (Kinematica AG, Lucerne, Switzerland) at 10,000 rpm (high-shear mixing). The solution was further emulsified using a Microfluidizer (Microfluidics [Newton, Mass.] model M-110L F12Y with ice bath and cooling coil), with an inlet pressure of 80 psi, for 4 minutes (high-pressure homogenization). The ethyl acetate was removed from the emulsion using a rotary evaporator, resulting in an aqueous suspension of nanoparticles.

Light Scattering Analysis

The particle size of the nanoparticles in the aqueous suspension was determined using dynamic light scattering (DLS) as follows. First, the aqueous suspension was filtered using a 1 µm glass membrane filter (Anatop filter, Whatman), and poured into a cuvette. Dynamic light-scattering was measured using a Brookhaven Instruments (Holtsville, N.Y.) BI-200SM particle size analyzer with a BI-9000AT correlator. The sums of exponentials from the autocorrelation functions are analyzed to extract size distributions from the samples, and the size is reported as the cumulant value. The average diameter was found to be 114 nm, with a polydispersity of 0.03.

The aqueous suspension was allowed to stand unmixed for 3 days (ambient conditions) to measure stability. DLS analysis showed that the average cumulant diameter of the nanoparticle suspension after 3 days was 117 nm, with a polydispersity of 0.06. These results demonstrate that the nanoparticle suspensions are stable for at least 3 days with no measurable particle agglomeration.

Free Drug Analysis

The amount of free drug provided by a suspension of the nanoparticles of Example 1 was measured using the following procedure. The nanoparticle suspension was centrifuged for 3 minutes at 13,000 rpm using a 30,000-dalton molecular-weight cutoff centrifuge tube filter, and 50 µL of the supernatant was added to 250 µL acetonitrile. The sample was assayed by HPLC. As shown in Table 3, the nanoparticle suspension provided a free drug concentration that is 7.9-fold that provided by bulk Drug 1.

TABLE 3

| Suspension Sample | Free Drug (µg/mL) |
|---|---|
| Bulk Drug 1 | 11 |
| Nanoparticles of Example 1 | 87 |

Control 1

As a control, nanoparticles were prepared containing Drug 1 and the poorly aqueous soluble non-ionizable cellulosic polymer ethylcellulose, but without an amphiphilic non-ionizable block copolymer. To form Control 1 nanoparticles, 40.6 mg Drug 1 and 123.8 mg ethylcellulose were dissolved in 5 mL methylene chloride to form an organic solution. The organic solution was then poured into 20 mL deionized water, and emulsified as described in Example 1. The methylene chloride was removed from the emulsion using a rotary evaporator, resulting in an aqueous suspension of nanoparticles. The aqueous suspension was analyzed using DLS as described in Example 1. The cumulant diameter of the nanoparticles was 815 nm, with a polydispersity of 0.41. Visual observation of the aqueous suspension confirmed large agglomerated and stringy material. These results show that nanoparticles made without an amphiphilic non-ionizable block copolymer did not provide a stable formulation.

Example 2

Nanoparticles containing Drug 2 were prepared using a precipitation method as follows. First, a water-miscible organic solution was formed by dissolving 250.9 mg Drug 2, 517.0 mg ethylcellulose, and 250.4 mg pCL-PEG in 100 mL tetrahydrofuran (THF). The organic solution was mixed using a vortex mixer for 10 seconds. To form the nanoparticles, a glass pipette containing the organic solution was inserted under the surface of an aqueous solution consisting of 900 mL of filtered water, and delivered into the stirring vortex all at once, rapidly forming nanoparticles. The THF was removed from the suspension using a rotary evaporator (40° C., 200 rpm, 30 min), resulting in an aqueous suspension of nanoparticles.

Light Scattering Analysis

The aqueous suspension of Example 2 was filtered using a 1 µm glass membrane filter, and analyzed using DLS. The average cumulant diameter of the nanoparticles in aqueous suspension was 113 nm, with a polydispersity of 0.11.

The concentration of nanoparticles in the aqueous suspension was increased using tangential flow filtration as follows. The aqueous suspension was pumped to a Pellicon® XL Filter containing a Biomax® 300K polyethersulfone membrane (available from Millipore Corporation, Bellerica, Mass.). The membrane allowed the aqueous solution to pass through while retaining the nanoparticles. The volume of the aqueous suspension was reduced such that the concentration of Drug 2 in the aqueous solution was about 8.2 mg/mL as determined using HPLC analysis. Deionized water was then added to this concentrated solution to form an aqueous suspension containing 5 mg/mL of Drug 2.

In Vivo Evaluation of Nanoparticles of Example 2

The nanoparticle suspension of Example 2 was tested in vivo in male Sprague-Dawley rats (n=20). The aqueous nanoparticle suspension (5 mg/mL potency of Drug 2; 10 mg/kg dose) was administered orally to fed rats via a ball-tipped gavage needle. Following oral dose administration, blood (approximately 2 mL) was collected from 4 animals/timepoint at 1, 2, 4, 6, and 8 hours postdose. Blood was collected via jugular venipuncture and transferred into tubes containing potassium EDTA anticoagulant.

Blood was maintained on wet ice prior to centrifugation to obtain plasma. Centrifugation began within 1 hour of collection, and samples were centrifuged at 2500 rpm for 15 minutes. Plasma was maintained on dry ice prior to storage at approximately −70° C. Plasma was analyzed using liquid chromatography with tandem mass spectrometry (LC/MS/MS). The results are shown in Table 4.

TABLE 4

| Time (hr) | Drug 2 Conc. (ng/mL) |
|---|---|
| predose | BLQ* |
| 1 | 758 |
| 2 | 994 |
| 4 | 939 |

TABLE 4-continued

| Time (hr) | Drug 2 Conc. (ng/mL) |
|---|---|
| 6 | 598 |
| 8 | 392 |

BLQ = Below the limit of quantitation (3.91 ng/mL)

Example 3

Nanoparticles containing Drug 2 were prepared using a precipitation method as follows. A water-miscible organic solution was formed by dissolving 1.2514 g Drug 2, 2.5015 g ethylcellulose, and 1.2517 g pCL-PEG in 500 mL THF. The organic solution was mixed and added to 1.5 L aqueous solution, as described in Example 3. The solvent was removed by rotary evaporation, resulting in an aqueous suspension of nanoparticles.

Light Scattering Analysis

The aqueous suspension of Example 3 was filtered using a 1 μm glass membrane filter, and analyzed using DLS. The average cumulant diameter of the nanoparticles in aqueous suspension was 115 nm, with a polydispersity of 0.21.

A smaller batch of nanoparticle suspension was made using this precipitation method as described above (with 1 mL organic solution into 9 mL water). DLS analysis 18 hours after the nanoparticle suspension was formed showed that the average cumulant diameter was 135 nm, with a polydispersity of 0.20. The suspension was allowed to stand unmixed for 5 days (ambient conditions) and the particle size was determined by DLS to be 130 nm, with a polydispersity of 0.20. These results demonstrate that the nanoparticle suspension of Example 3 was stable for at least 5 days with no significant particle agglomeration.

Free Drug Analysis

The amount of free drug provided by the nanoparticles of Example 3 was measured using nuclear magnetic resonance (NMR). For this test, a suspension containing 4.0 mg of the nanoparticles of Example 3 was added to Eppendorf tubes (in duplicate) containing 1.0 mL of deuterated phosphate-buffered saline (PBS), pH 6.5, containing 2 wt % of a 4/1 mixture of sodium taurocholic acid and 1-palmitoyl-2-oleyl-sn-glycero-3-phosphocholine (NaTC/POPC). The solution also contained 0.11 mg 3-(trimethylsilyl)propionic-2,2,3,3-$d_4$ acid, sodium salt ("TSP"; a deuterated NMR reference standard). An internal standard solution of trifluoroacetic acid (TFA) was added to the tubes to give a concentration of 0.8976 mM $^{19}$F. After adding the deuterated NaTC/POPC solution, the tubes were vortexed 1 minute, and allowed to stand undisturbed overnight in a 37° C. controlled temperature chamber. Prior to sampling, an aliquot was centrifuged to remove drug particulates. The supernatant was then carefully transferred to an 8 mm glass NMR tube. Crystalline Drug 2 alone was tested for comparison.

Fluorine spectra of the samples were recorded at 282.327 MHz on a Varian Gemini 2000, 300 MHz NMR equipped with a Nalorac 8 mm indirect detection probe. The sample temperature was maintained at 37° C. in the probe. Drug resonances were integrated relative to the internal standard peak and the drug concentration determined.

As shown in Table 5, the nanoparticle suspension of Example 3 provided a free drug concentration that is 2.4-fold the free drug concentration provided by crystalline drug alone.

TABLE 5

| Suspension Sample | Free Drug (μg/mL) |
|---|---|
| Example 3 | 19 |
| Crystalline Drug 2 alone | 8 |

The concentration of nanoparticles in the aqueous suspension was increased using tangential flow filtration as described for Example 2 except that the membrane used was a Pellicon® XL Filter containing a PLCGC® 10K regenerated cellulose membrane (available from Millipore Corporation, Bellerica, Mass.). The concentrated sample was adjusted such that the concentration of Drug 2 in the nanoparticle suspension was 1.9 mg/mL. The particle size of the concentrated nanoparticle suspension was 122 nm, with a polydispersity of 0.21, as measured by DLS.

In Vivo Evaluation of Nanoparticles of Example 3

The nanoparticles of Example 3 were evaluated in vivo. Samples were dosed orally as a suspension to 6 male beagle dogs. Animals were fasted overnight (10 hours predose) through at least 12 hours postdose. Approximately 50 mL of the nanoparticle suspension (10 mg Drug 2/kg) was administered to each dog. The dose was administered via oral gavage, followed by approximately 5 mL water. Whole-blood samples (3-mL red-top Vacutainer tubes without serum separators) were taken from the jugular vein before dosing and at 0.5, 1, 1.5, 2, 2.5, 3, 3.5, 4, 4.5, 5, 5.5, 6, 6.5, 7, 7.5, 8, 12, and 24 hours postdose. Serum was harvested into tubes containing $K_2$EDTA anticoagulant. Blood was maintained on wet ice prior to centrifugation to obtain plasma. Centrifugation began within 1 hour of collection, and samples were centrifugation at 2500 rpm for 15 minutes. Plasma was maintained on dry ice prior to storage at approximately −70° C. Plasma was analyzed using liquid chromatography with tandem mass spectrometry (LC/MS/MS). The results are shown in Table 6.

TABLE 6

| Parameter | Example 3 Nanoparticle Suspension |
|---|---|
| $C_{max}$ (ng/mL) | 649 |
| $T_{max}$ (hours) | 1.33 |
| $AUC_{0-t}$ (ng/mL-hr) | 2780 |

Isolation of a Solid Composition of Example 3

A solid composition containing nanoparticles made using the procedures of Example 3 was isolated using the following procedure. First, the nanoparticle suspension was concentrated about 5 fold using tangential flow filtration as described for Example 2. The concentrated aqueous suspension was then pumped into a spray-drying apparatus at a rate of 0.15 mL/min. Heated gas entered the chamber at an inlet temperature of 120° C., with a flow of 1 SCFM. The resulting solid nanoparticles were collected on a 0.8 μm nylon filter.

PXRD Evaluation

The solid composition containing nanoparticles made using the procedure of Example 3 were examined using powder x-ray diffraction (PXRD) with a Bruker AXS D8 Advance diffractometer to determine the amorphous character of the drug in the nanoparticles. Approximately 30 mg of sample was packed in a Lucite sample cup fitted with a Si(511) plate as the bottom of the cup to give no background signal. The sample was spun in the φ plane at a rate of 30 rpm to minimize crystal orientation effects. The x-ray source (KCu$_\alpha$, λ=1.54 Å) was operated at a voltage of 45 kV and a current of 40 mA. Data were collected over a period of 27 minutes in continuous detector scan mode at a scan speed of 1.8 seconds/step and a step size of 0.04°/step. Diffractograms were collected over the 2θ range of 7° to 19°. FIG. 1 shows the diffraction pattern of the solid composition of Example 3, as well as the diffraction pattern for crystalline Drug 2 and pCL-PEG alone. The pattern for the solid composition of Example 3 shows two peaks: one at about 21 degrees 2θ, the other at about 24 degrees 2θ. Comparison of these peaks with the diffraction pattern for pCL-PEG shows that these peaks correspond to crystalline pCL-PEG present in the solid composition, and not to crystalline drug. Thus, these data indicate that the drug in the solid composition of Example 3 is in non-crystalline form.

Example 4

Nanoparticles containing Drug 2 were prepared using a precipitation method as follows. A water-miscible organic solution was formed by dissolving 40.5 mg Drug 2, 40.4 mg ethylcellulose, and 41.0 mg pCL-PEG in 12 mL THF. The organic solution was mixed and added to 90 mL aqueous solution, as described in Example 2. The solvent was removed by rotary evaporation, resulting in an aqueous suspension of nanoparticles.

Light Scattering Analysis

The aqueous suspension of Example 4 was filtered using a 1 μm glass membrane filter, and analyzed using DLS. The average cumulant diameter of the nanoparticles in aqueous suspension was 146 nm with a polydispersity of 0.12. The suspension was allowed to stand unmixed for 14 days (ambient conditions) and the particle size was determined by DLS to be 141 nm, with a polydispersity of 0.13. These results demonstrate that the nanoparticle suspension of Example 4 was stable for at least 14 days with no significant particle agglomeration.

Control 2

Control 2 nanoparticles were made for comparison to Example 4. Nanoparticles of Drug 2 and pCL-PEG, that did not contain the non-ionizable cellulosic polymer ethylcellulose, were prepared using a precipitation method as follows. A water-miscible organic solution was formed by dissolving 50.0 mg Drug 2 and 49.7 mg pCL-PEG in 10 mL THF. The organic solution was mixed and added to 18 mL aqueous solution, as described in Example 2. The solvent was removed by rotary evaporation, resulting in an aqueous suspension of nanoparticles.

Light Scattering Analysis

The Control 2 aqueous suspension was filtered using a 1 μm glass membrane filter, and analyzed using DLS. The average cumulant diameter of the nanoparticles was 49.1 nm, with a polydispersity of 0.27. The suspension was allowed to stand unmixed for 2 days (ambient conditions) and based on visual observation, particles were agglomerating and precipitating. These results demonstrate that the Control 2 nanoparticles (without a non-ionizable cellulosic polymer) are less stable than the nanoparticles of the invention (Example 4).

Example 5

Nanoparticles containing celecoxib ("Drug 3") were prepared using the emulsion process described in Example 1 with the following exceptions. The organic solution consisted of 21.5 mg celecoxib, 50.0 mg ethylcellulose, and 21.1 mg pCL-PEG dissolved in 4 mL ethyl acetate. The organic solution was poured into the aqueous solution and emulsified as described for the nanoparticles of Example 1. The ethyl acetate was removed from the emulsion using a rotary evaporator, resulting in an aqueous suspension of nanoparticles.

Light Scattering Analysis

The aqueous suspension above was filtered using a 1 μm glass membrane filter and analyzed using DLS. The average cumulant diameter was found to be 139 nm, with a polydispersity of 0.13.

The aqueous suspension above was allowed to stand unmixed for 1 day (ambient conditions) to measure stability. DLS analysis showed that the average cumulant diameter of the nanoparticle suspension after 1 day was 146 nm with a polydispersity of 0.11. These results demonstrate that the nanoparticle suspensions are stable for at least 1 day with no measurable particle agglomeration.

Example 6

Nanoparticles containing Drug 2 were prepared using a precipitation method as follows. A water-miscible organic solution was formed by dissolving 5 mg Drug 2, 35 mg ethylcellulose, and 10 mg pCL-PEG in 5 mL 4/1 (v/v) acetone/ethyl acetate. The organic solution was mixed and added to 45 mL aqueous solution, as described in Example 2. The solvent was removed by rotary evaporation, resulting in an aqueous suspension of nanoparticles. The aqueous suspension was analyzed by DLS and the average cumulant diameter was 116 nm with a polydispersity of 0.5.

Example 7

Nanoparticles containing Drug 2 were prepared using a precipitation process as described above. The organic solution consisted of 24.2 mg Drug 2, 76.7 mg of the poorly aqueous soluble non-ionizable cellulosic polymer cellulose acetate (CA 398-10NF, Eastman Chemical Co., Kingsport, Tenn.), and 24.8 mg pCL-PEG, dissolved in 10 mL acetone. A 1-mL sample of the organic solution was rapidly added into the stirring vortex of 9 mL aqueous solution. The acetone was removed using a rotary evaporator, resulting in an aqueous suspension of nanoparticles, with a composition ratio of 19:61:20 Drug 2:cellulose acetate:pCL-PEG. DLS analysis showed that the average cumulant diameter of the nanoparticles was 120 nm, with a polydispersity of 0.26.

Example 8

Nanoparticles containing Drug 2 were prepared using a precipitation process. The organic solution consisted of 24.9 mg Drug 2, 53.3 mg of a poorly aqueous soluble non-ionizable cellulosic polymer cellulose acetate butyrate (CAB-551-0.01, Eastman Chemical Co.), and 26.0 mg of a the amphiphilic non-ionizable block copolymer poly(DL-lactide-co-glycolide 50:50)-polyethylene glycol (PLGA-PEG;

RESOMER® PEG, PLGA diblock copolymer with 15% PEG 5000, Boehringer Ingelheim in Ingelheim, Germany), in 10 mL acetone. A 1-mL sample of the organic solution was rapidly added into the stirring vortex of 9 mL aqueous solution. The acetone was removed using a rotary evaporator, resulting in an aqueous suspension of nanoparticles, with a composition ratio of 24:51:25 Drug 2:CAB:PLGA-PEG. DLS analysis showed that the average cumulant diameter was 84 nm, with a polydispersity of 0.08.

Control 3

Nanoparticles were prepared containing Drug 1, a poorly aqueous soluble non-ionizable polymer that is not a cellulosic polymer, and an amphiphilic non-ionizable block copolymer. The nanoparticles of Control 3 were made using a precipitation process as described above. The organic solution consisted of 35.4 mg Drug 1, 33.6 mg poly(DL-lactide-co-glycolide 50:50) (PLGA 502H; RESOMER®, Boehringer Ingelheim), and 33.4 mg pCPEG in 10 mL acetone. A 1-mL sample of the organic solution was rapidly added into the stirring vortex of 9 mL aqueous solution. The acetone was removed using a rotary evaporator, resulting in an aqueous suspension of nanoparticles, with a composition ratio of 34:33:33 Drug 1:PLGA:pCL-PEG. DLS analysis showed that the average cumulant diameter was 1273 nm, with a polydispersity of 0.48. Visual observation of the aqueous suspension confirmed large agglomerated material.

Control 4

Nanoparticles were prepared containing Drug 1, with a non-ionizable non-cellulosic polymer that is soluble in aqueous solution, and an amphiphilic non-ionizable block copolymer. The nanoparticles of Control 4 were made using a precipitation process. The organic solution consisted of 31.4 mg Drug 1, 33.8 mg polyvinyl pyrrolidone (PVP K29/32, ISP Technologies, Wayne, N.J.), and 32.3 mg pCL-PEG in 10 mL acetone. A 1-mL sample of the organic solution was rapidly added into the stirring vortex of 9 mL aqueous solution. The acetone was removed using a rotary evaporator, resulting in an aqueous suspension of nanoparticles, with a composition ratio of 32:35:33 Drug 1:PVP:pCL-PEG.

DLS analysis showed that the average cumulant diameter was 5206 nm, with a polydispersity of 1.11. Visual observation of the aqueous suspension confirmed large agglomerated material.

Control 5

Nanoparticles were prepared containing Drug 1, with a non-ionizable non-cellulosic polymer that is soluble in aqueous solution, and a non-ionizable material that is also soluble in aqueous solution. The nanoparticles of Control 5 were made using a precipitation process. The organic solution consisted of 35.4 mg Drug 1, 32.2 mg PVP, and 44.2 mg polyethylene glycol 8000 (available from Spectrum Chemical, Gardena, Calif.), in 10 mL methanol. A 1-mL sample of the organic solution was rapidly added into the stirring vortex of 9 mL aqueous solution. The methanol was removed using a rotary evaporator, resulting in an aqueous suspension of nanoparticles, with a composition ratio of 32:29:39 Drug 1:PVP:PEG 8000.

DLS analysis showed that the average cumulant diameter was 3362 nm, with a polydispersity of 0.88. Visual observation of the aqueous suspension confirmed large agglomerated material.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A pharmaceutical composition comprising nanoparticles, said nanoparticles consisting of:
   (a) a drug having a solubility in water of less than 5 mg/mL over the pH range of 6.5 to 7.5 at 25° C., at least 90 wt % of said drug being non-crystalline;
   (b) a poorly aqueous soluble non-ionizable cellulosic polymer selected from the group consisting of ethylcellulose, cellulose acetate, cellulose propionate, cellulose butyrate, cellulose acetate butyrate, and mixtures thereof; and
   (c) a poorly aqueous soluble polymeric amphiphilic non-ionizable block copolymer, wherein the amphilphilic non-ionizable copolymer is poly(ethylene oxide-b-ϵ-caprolactone);
   wherein said nanoparticles have an average size of less than 500 nm; and comprise from 1 wt % to 80 wt % said drug, from 10 wt % to 75 wt % said non-ionizable cellulosic polymer, and from 5 wt % to 60 wt % said amphiphilic non-ionizable block copolymer.

2. The composition of claim 1 wherein said nanoparticles are in the form of a core comprising said drug and said non-ionizable cellulosic polymer.

3. The composition of claim 2 wherein said core further comprises said amphilphillic non-ionizable block copolymer.

4. The composition of claim 1 wherein said nanoparticles have the following composition: from 5 wt % to 50 wt % said drug, from 30 wt % to 70 wt % said non-ionizable cellulosic polymer, and from 5 wt % to 30 wt % said amphiphillic non-ionizable block copolymer.

5. The composition of claim 1 wherein said nanoparticles have an average size of less than 300 nm.

6. The composition of claim 1 wherein said non-ionizable cellulosic polymer is ethylcellulose and said amphiphillic non-ionizable block copolymer is poly(ethylene oxide-b-ϵ-caprolactone).

7. A pharmaceutical composition comprising an aqueous suspension of the nanoparticles of claim 1.

8. A process for forming nanoparticle of claim 1, comprising:
   (a) forming an organic solution consisting a drug and a poorly aqueous soluble non-ionizable cellulosic polymer dissolved in a solvent, wherein said drug has solubility in water of less than 5 mg/mL over the pH range of 6.5 to 7.5 at 25° C. and said poorly aqueous soluble non-ionizable cellulosic polymer, selected from the group consisting of ethylcellulose, cellulose acetate, cellulose propionate, cellulose butyrate, cellulose acetate butyrate, and mixtures thereof;
   (b) forming an aqueous solution;
   (c) adding a poorly aqueous soluble polymeric amphiphilic non-ionizable block copolymer selected from poly(ethylene oxide-b-ϵ-caprolactone)to at least one of said organic solution and said aqueous solution;
   (d) mixing said organic solution with said aqueous solution to form a first mixture; and
   (e) removing said solvent from said mixture to form a suspension comprising said nanoparticles and said aqueous solution, wherein (i) said nanoparticles have an average size of less than 500 nm; (ii) at least 90 wt % of said drug in said nanoparticles is noncrystalline; and (iii) said drug, said non-ionizable cellulosic polymer, and said amphiphilic non-ionizable block copolymer collectively constitute at least 60 wt % of said nanoparticles.

9. The process of claim 8 further comprising an additional step of (f) adding a matrix material to said suspension.

10. The process of claim 9 wherein said matrix material is selected from the group consisting of polyvinyl pyrrolidone, trehalose, hydroxypropyl methyl cellulose, hydroxypropyl cellulose, casein, caseinate, albumin, gelatin, acacia, lactose, mannitol, pharmaceutically acceptable forms thereof, and mixtures thereof.

11. The process of claim 8 further comprising an additional step (g) of removing liquid from said suspension to form a solid composition.

12. The process of claim 11 wherein said liquid is removed by at least one process selected from the group consisting of spray drying, spray coating, spray layering, lyophylization, evaporation, vacuum evaporation, and filtration.

13. The process of claim 11 wherein said liquid is removed by spray drying.

\* \* \* \* \*